(12) United States Patent
Manginell et al.

(10) Patent No.: US 10,197,532 B1
(45) Date of Patent: Feb. 5, 2019

(54) MINIATURIZED PULSED DISCHARGE IONIZATION DETECTOR, NON-RADIOACTIVE IONIZATION SOURCES, AND METHODS THEREOF

(71) Applicant: National Technology & Engineering Solutions of Sandia, LLC, Albuquerque, NM (US)

(72) Inventors: Ronald P. Manginell, Albuquerque, NM (US); Matthew W. Moorman, Albuquerque, NM (US); Kent B. Pfeifer, Los Lunas, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 42 days.

(21) Appl. No.: 14/992,855

(22) Filed: Jan. 11, 2016

Related U.S. Application Data

(60) Provisional application No. 62/102,178, filed on Jan. 12, 2015, provisional application No. 62/195,933, filed on Jul. 23, 2015.

(51) Int. Cl.
*G01N 27/70* (2006.01)
*H05K 3/32* (2006.01)

(52) U.S. Cl.
CPC .............. *G01N 27/70* (2013.01); *H05K 3/32* (2013.01); *H05K 2203/166* (2013.01)

(58) Field of Classification Search
CPC ..... G01N 27/70; H05K 3/22; H05K 2203/166
See application file for complete search history.

(56) References Cited

U.S. PATENT DOCUMENTS

| | | | | |
|---|---|---|---|---|
| 2,814,024 A | * | 11/1957 | Narozny | H01R 12/58 439/58 |
| 5,767,683 A | * | 6/1998 | Stearns | G01N 27/70 324/449 |
| 6,444,326 B1 | | 9/2002 | Smith | |
| 6,666,907 B1 | | 12/2003 | Manginell et al. | |
| 6,699,392 B1 | | 3/2004 | Manginell et al. | |
| 6,902,701 B1 | | 6/2005 | Hughes et al. | |
| 7,078,237 B1 | | 7/2006 | Mowry et al. | |
| 7,155,812 B1 | * | 1/2007 | Peterson | H01C 3/06 250/286 |

(Continued)

FOREIGN PATENT DOCUMENTS

| | | |
|---|---|---|
| WO | WO 00/57182 A1 | 9/2000 |
| WO | WO 2009/045116 A1 | 4/2009 |

OTHER PUBLICATIONS

U.S. Appl. No. 14/945,274, filed Nov. 18, 2015, Moorman et al.

(Continued)

*Primary Examiner* — Julian Huffman
*Assistant Examiner* — Michael Konczal
(74) *Attorney, Agent, or Firm* — Helen S. Baca

(57) ABSTRACT

The present application relates to pulsed discharge ionization detectors (PDIDs) and non-radioactive ionization sources, including miniaturized forms thereof. In some examples, the PDID includes annular electrodes, where each electrode is disposed between annular insulators. Also provided herein are methods of making and using such PDIDs, such as for detecting one or more volatile organic compounds, as well as non-radioactive ionization sources.

27 Claims, 15 Drawing Sheets

(56) References Cited

U.S. PATENT DOCUMENTS

| | | | |
|---|---|---|---|
| 7,417,222 B1* | 8/2008 | Pfeifer | H01J 49/0027 250/282 |
| 7,697,134 B1 | 4/2010 | Sinclair et al. | |
| 7,708,943 B1 | 5/2010 | Robinson et al. | |
| 7,913,534 B1* | 3/2011 | Robinson | G01N 35/00693 73/1.06 |
| 8,123,841 B2 | 2/2012 | Masel et al. | |
| 8,296,078 B1 | 10/2012 | Pfeifer et al. | |
| 8,298,488 B1 | 10/2012 | Lewis et al. | |
| 8,518,663 B2 | 8/2013 | Trevejo et al. | |
| 8,736,000 B1 | 5/2014 | Manginell et al. | |
| 9,472,689 B1 | 10/2016 | Elizondo-Decanini et al. | |
| 2007/0256938 A1* | 11/2007 | Fruth | B23H 3/00 205/668 |
| 2008/0286830 A1 | 11/2008 | Scotter et al. | |
| 2009/0230300 A1 | 9/2009 | Trevejo et al. | |
| 2014/0053627 A1* | 2/2014 | Stearns | G01N 30/64 73/23.4 |
| 2014/0145724 A1* | 5/2014 | Shinada | G01N 30/64 324/464 |

OTHER PUBLICATIONS

U.S. Appl. No. 14/992,871, filed Jan. 11, 2016, Moorman et al.
Achyuthan KE et al., "Design considerations for high-throughput screening and in vitro diagnostic assays," *Comb. Chem. High Throughput Screen.* Jul. 2007;10(6):399-412.
Adamovics JA et al., "Gas Chromatography," Chapter 4 in *Chromatographic analysis of pharmaceuticals*, 2nd edition, Adamovics JA (ed.), 1997, Marcel Dekker, Inc., New York, NY, pp. 79-134.
Akutsu T et al., "Individual comparisons of the levels of (E)-3-methyl-2-hexenoic acid, an axillary odor-related compound, in Japanese," *Chem. Senses* May 2006;31:557-63.
Allardyce RA et al., "Detection of volatile metabolites produced by bacterial growth in blood culture media by selected ion flow tube mass spectrometry (SIFT-MS)," *J. MicrobioL Meth.* 2006;65:361-5.
Anderson JM et al., "Isothermal mass flow measurements in microfabricated rectangular channels over a very wide Knudsen range," *J. Micromech. Microeng.* 2014;24(5):055013 (13 pp.).
Bhushan A et al., "Hybrid integration of injector and detector functions for microchip gas chromatography," *Analyst* 2010; 135:2730-6.
Biet F et al., "Zoonotic aspects of *Mycobacterium bovis* and *Mycobacterium avium-intracellulare* complex (MAC)," *Vet. Res.* 2005;36:411-36.
Bostaris G et al., "Rapid detection methods for viable *Mycobacterium avium* subspecies *paratuberculosis* in milk and cheese," *Int. J. Food Microbiol.* 2010;141:S87-90.
Bunge M et al., "On-line monitoring of microbial volatile metabolites by proton transfer reaction-mass spectrometry," *Appl Environ. Microbiol.* Apr. 2008;74(7):2179-86.
Cai H et al., "Pulsed discharge helium ionization detector with multiple combined bias/collecting electrodes for gas chromatography," *J. Chromatogr. A* 2013;1284:163-73.
Cai H et al., "Characterization of the pulsed discharge electron capture detector," *Anal. Chem.* 1996;68(7):1233-44.
Dahl DA, "SIMION for the personal computer in reflection," *Int. J. Mass Spectrom.* 2000;200:3-25.
Dahl DA et al., "Comparison of ion trajectories in vacuum and viscous environments using SIMION: Insights for instrument design," *Int. J. Mass Spectrom.* 2007;266:156-65.
Dolch ME et al., "Volatile compound profiling for the identification of Gram-negative bacteria by ion-molecule reaction-mass spectrometry," *J. Appl. Microbiol.* 2012;113:1097-105.
Filipiak W et al., "Molecular analysis of volatile metabolites released specifically by *Staphylococcus aureus* and *Pseudomonas aeruginosa*," *BMC Microbiol.* 2012;12:113 (16 pp.).
Forsyth DS, "Pulsed discharge detector: theory and applications," *J. Chromatogr. A* 2004;1050:63-8.
Forsyth DS et al., "Detection of organotin, organomercury, and organolead compounds with a pulsed discharge detector (PDD)," *Anal. Bioanal. Chem.* 2002;374:344-7.
Galambos P et al., "Active MEMS valves for flow control in a high-pressure micro-gas-analyzer," *J. Microelectromech. Sys.* Oct. 2011;20(5):1150-62.
Gibson T et al., "Not to be sniffed at," *Microbiol. Today* Feb. 2000;27:14-7.
Gordon SG et al., "Studies of trans-3-methyl-2-hexenoic acid in normal and schizophrenic humans," *J. Lipid Res.* 1973;14:495-503.
Gremaud G et al., "Windowless pulsed-discharge photoionization detector application to qualitative analysis of volatile organic compounds," *J. Chromatogr. A* 1996;724:235-50.
Grob K et al., "Testing capillary gas chromatographic columns," *J. Chromatogr.* 1981;219:13-20.
Grob K, Jr. et al., "Comprehensive, standardized quality test for glass capillary columns," *J. Chromatogr.* 1978;156:1-20.
Harris NB et al., "Recovery of *Mycobacterium bovis* from soft fresh cheese originating in Mexico," *Appl. Environ. Microbiol.* Feb. 2007;73:1025-8.
Holmes SM, "Researching new detectors for chemical, biological threats," *Sandia Lab News* Aug. 9, 2013, p. 11.
Jünger M et al., "Ion mobility spectrometry for microbial volatile organic compounds: A new identification tool for human pathogenic bacteria," *Appl. Microbiol. Biotechnol.* Mar. 2012;93(6):2603-14.
Lai H et al., "The predictive power of SIMION/SDS simulation software for modeling ion mobility spectrometry instruments," *Int. J. Mass Spectrom.* 2008;276:1-8.
Laurens JB et al., "Gas chromatographic analysis of trace gas impurities in tungsten hexafluoride," *J. Chromatogr. A* 2001;911:107-12.
Lewis AC et al., "Microfabricated planar glass gas chromatography with photoionization detection," *J. Chromatogr. A* 2010;1217:768-74.
Lewis PR et al., "Recent advancements in the gas-phase MicroChemLab," *IEEE Sens. J.* Jun. 2006; 6(3):784-95.
Mainelis G et al., "Performance characteristics of the aerosol collectors of the Autonomous Pathogen Detection System (APDS)," *Aerosol Sci. Technol.* 2005;39:461-71.
Manginell RP et al. "Development of a mesoscale pulsed discharge helium ionization detector for portable gas chromatography," *Anal. Sci.* 2015;31(11):1183-8.
Manginell RP et al., "Diagnostic potential of the pulsed discharged helium ionization detector (PDHID) for pathogenic Mycobacterial volatile biomarkers," *J. Breath Res.* 2013;7:037107 (9 pp.).
Manginell RP et al., "Mass-sensitive microfabricated chemical preconcentrator," *J. Microelectromech. Sys.* Dec. 2008;17(6):1396-407.
Manginell RP et al., "A monolithically-integrated μGC chemical sensor system," *Sensors* 2011;11:6517-32.
Manginell RP et al., "A materials investigation of a phase-change micro-valve for greenhouse gas collection and other potential applications," *Rev. Sci. Instrum.* 2012;83:031301 (11 pp.).
Manginell RP et al., "Finite element modeling of a microhotplate for microfluidic applications," Proceedings of Modeling and Simulation of Microsystems (MSM '99), San Juan, PR, USA, 1999, 663 (6 pp.).
McNerney R et al., "Production of volatile organic compounds by mycobacteria," *FEMS Microbiol. Lett.* 2012;328:150-6.
Narayanan S et al., "A micro-discharge photoionization detector for micro-gas chromatography," *Microchim. Acta* 2014;181(5):493-99.
Narayanan S et al., "Characterization of a micro-helium discharge detector for gas chromatography," *Sens. Actuat. B* 2015;206:190-7.
Novelli PC et al., "Application of gas chromatography with a pulsed discharge helium ionization detector for measurements of molecular hydrogen in the atmosphere," *Environ. Sci. Technol.* 2009;43(7):2431-6.
Ohira S et al., "Micro gas analyzers for environmental and medical applications," *Anal. Chim. Acta* 2008;619(2):143-56.
Roberge MT et al., "Evaluation of the pulsed discharge helium ionization detector for the analysis of hydrogen and methane in breath," *J. Chromatogr. A* 2004;1027:19-23.

(56) References Cited

OTHER PUBLICATIONS

Ross BM et al., "Stability of methylnicotinate in aqueous solution as utilized in the 'niacin patch test'," *BMC Res. Notes* Sep. 2008;1:89 (5 pp.).

Sandia National Laboratories, "Laboratory Directed Research and Development Annual Report 2011," Sandia Report No. SAND 2012-2254P, Mar. 2012, pp. 3-20 and 527-529 (23 pages).

Sandia National Laboratories, News Release, "Researching new detectors for chemical, biological threats," Sep. 5, 2013 (4 pp.).

Senecal AG et al., "Rapid detection of pathogenic bacteria by volatile organic compound (VOC) analysis," *Proc. SPIE* 2002;4575:121-31.

Spooner AD et al., "Evaluation of a combination of SIFT-MS and multivariate data analysis for the diagnosis of *Mycobacterium bovis* in wild badgers," *Analyst* 2009;134:1922-7.

Straus E et al., "Radioimmunoassay of tuberculoprotein derived from *Mycobacterium tuberculosis*," *Proc. Nat'l Acad. Sci. USA* Jul. 1980;77:4301-4.

Syhre M et al., "The scent of *Mycobacterium tuberculosis*—Part II breath," *Tuberculosis* 2009;89:263-6.

Syhre M et al. "The scent of *Mycobacterium tuberculosis*," *Tuberculosis* 2008;88:317-23.

Wentworth WE et al., "Pulsed discharge emission detector: an element-selective detector for gas chromatography," *J. Chromatogr. A* 2000;872:119-40.

Whiting JJ et al., "High-speed two-dimensional gas chromatography using microfabricated GC columns combined with nanoelectromechanical mass sensors," *Itn'l Solid-State Sensors, Actuators and Microsystems Conf.*, held on Jun. 21-25, 2009 in Denver, CO, pp. 1666-1669.

Winniford BL et al., "Universal and discriminative detection using a miniaturized pulsed discharge detector in comprehensive two-dimensional GC," *J. Sep. Sci.* 2006;29:2664-70.

Zhu J et al., "Fast detection of volatile organic compounds from bacterial cultures by secondary electrospray ionization-mass spectrometry," *J. Clin. Microbiol.* 2010;48:4426-31.

\* cited by examiner

FIG. 5A                                    FIG. 5B

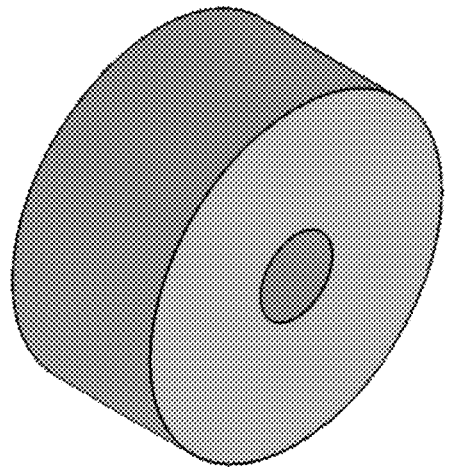
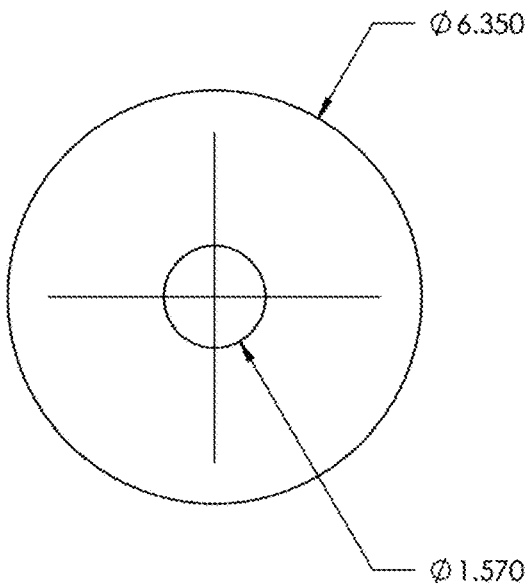
FIG. 6A  FIG. 6B
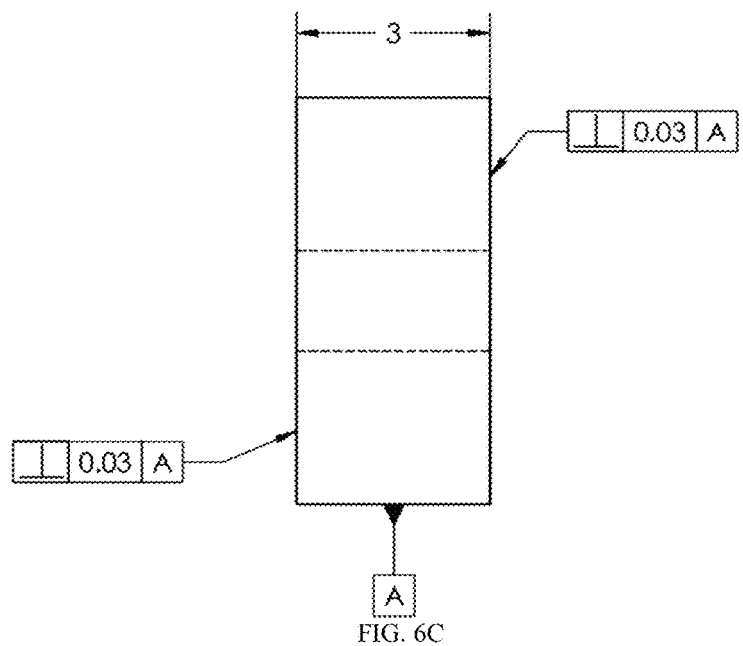
FIG. 6C

MINIATURIZED PULSED DISCHARGE IONIZATION DETECTOR, NON-RADIOACTIVE IONIZATION SOURCES, AND METHODS THEREOF

CROSS-REFERENCE TO RELATED APPLICATION

This application claims priority to U.S. Provisional Patent Application No. 62/102,178, filed on Jan. 12, 2015 under the title, "MINIATURIZED PULSED DISCHARGE IONIZATION DETECTOR, NON-RADIOACTIVE IONIZATION SOURCES, AND METHODS THEREOF," and claims priority to U.S. Provisional Patent Application No. 62/195,933, filed on Jul. 23, 2015 under the title, "DEVELOPMENT OF A MESOSCALE PULSED DISCHARGE HELIUM IONIZATION DETECTOR FOR PORTABLE GAS CHROMATOGRAPHY". Both applications are incorporated herein by reference in their entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD

The present application relates to pulsed discharge ionization detectors (PDIDs), such as miniaturized forms thereof. Also provided herein are non-radioactive ionization sources, as well as methods of making and using such PDIDs.

BACKGROUND

Vapor detection of chemical warfare agents (CWA), toxic industrial compounds (TICs), solvents, fixed/permanent gases, explosives, greenhouse gases (GHG), water contaminants, etc. is commonly conducted with laboratory equipment and some portable equipment. Growing bacteria, including ordinary pathogens and biological warfare agents (BWA), also produce volatile organic chemical (VOC) signatures in vivo or in vitro that can be detected in the lab by high-performance vapor methods. High-performance VOC detection methods can also sense signatures of human odor, human gender, and identity.

One platform for VOC detection includes a pulsed discharge ionization detector (PDID). Generally, the PDID includes a plasma discharge source, an inlet for analytes from a gas chromatography (GC) column, and an array of electrodes. PDID can be operated in various modes, such as a pulsed discharge helium ionization detector (PDHID) mode, a pulsed discharge electron capture detector (PDECD) mode, and a pulsed discharge emission detector (PDED) mode. In the PDHID mode, the PDID employs a pulsed DC discharge in a gas to photoionize analytes eluting from the GC column, and electrons released from this photoionization process are directed to the electrode array. Changes in measured current provide the measurable detector response.

PDIDs provide enhanced sensitivity and selectivity when coupled with GC platforms. Implementing PDIDs in the field requires further development. For instance, miniaturization of PDID and GC instruments for field applications mandates reducing size, weight, and power requirements. Thus, new miniaturized PDID devices and systems are needed.

SUMMARY

Accordingly, the present application relates to a miniaturized PDID device, as well as non-radioactive ionization sources. In particular embodiments, the present application describes a sensor capable of detecting any useful VOC (e.g., any herein) in a portable format with high sensitivity. Additional details follow.

Definitions

As used herein, the term "about" means+/−10% of any recited value. As used herein, this term modifies any recited value, range of values, or endpoints of one or more ranges.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microstructure" or "micro" is meant having at least one dimension that is less than 1 mm. For instance, a microstructure (e.g., any structure described herein) can have a length, width, height, cross-sectional dimension, circumference, radius (e.g., external or internal radius), or diameter that is less than 1 mm.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the application will be apparent from the following description and the claims.

BRIEF DESCRIPTION OF THE DRAWINGS

FIG. 1G is a cross-sectional view of the core after plasma discharge. FIG. 1H includes a dopant connector 1076.

FIG. 4B is a cross-sectional schematic of an exemplary PDID device. The expanded view shows the central core of the detector on the ceramic circuit board. Shown in FIG. 4B are details on the mini-PDID core and GC outlet position, where all measurements are provided in mm. The table at the lower right indicates the GC outlet position relative to the datum "A" in the schematic. Position '0' roughly corresponds to the centroid of the collector electrode. Position '−3' is slightly to the left of the leftmost bias electrode and was found to provide the best response using pentane as a model analyte.

FIG. 5A-5D provides schematics of an exemplary electrode in (A) perspective view, (B) cross-sectional view, along sectional line A-A in FIG. 5C, (C) plan view, and (D) side view. All measurements are provided in mm, unless otherwise indicated. FIG. 5A provides schematics of an exemplary electrode in a perspective view. FIG. 5B provides schematics of an exemplary electrode in a cross-sectional view. FIG. 5C provides schematics of an exemplary electrode in a plan view. FIG. 5D provides schematics of an exemplary electrode in a side view.

FIG. 6A-6C provides schematics of an exemplary insulator in (A) perspective view, (B) plan view, and (C) cross-sectional view. All measurements are provided in mm, unless otherwise indicated. FIG. 6A provides schematics of an exemplary insulator in perspective view. FIG. 6B provides schematics of an exemplary insulator in a plan view. FIG. 6C provides schematics of an exemplary insulator in a cross-sectional view.

FIG. 7A provides schematics of an exemplary positioner in a perspective view. FIG. 7B provides schematics of an exemplary positioner in a cross-sectional view along sectional line B-B. FIG. 7C provides schematics of an exemplary positioner in a perspective view along sectional line C-C. FIG. 7D provides schematics of an exemplary positioner in a plan view FIG. 8A-8C provides schematics of an exemplary port in (A) perspective view, (B) cross-sectional view, along sectional line B-B in FIG. 8A, and (C) cross-sectional view, along sectional line C-C in FIG. 8A. All measurements are provided in mm, unless otherwise indicated.

FIG. 9A provides schematics of another exemplary port in a bottom view. FIG. 9B provides schematics of another exemplary port in a perspective view. FIG. 9C provides schematics of another exemplary port in a cross-sectional view.

FIG. 10A provides schematics of an exemplary housing in a perspective view. FIG. 10B provides schematics of an exemplary housing in a cross-sectional view.

FIG. 11A provides schematic of an exemplary circuit in a side view. FIG. 11B provides schematic of an exemplary circuit in a top view. FIG. 11C provides schematic of an exemplary circuit in a bottom view.

DETAILED DESCRIPTION

We fabricated a miniPDID from stainless steel by photochemical etching and electroforming for rapid prototyping. Our electrode design enabled nesting of insulators. Thus, the detector core was self-aligned and compressed during assembly, facilitating miniaturization. The electrodes had a tang for insertion into standard circuit board spring connectors. In one non-limiting example, the miniPDID prototype was 80- and 40-fold smaller (in volume), as compared to other commercial standard or miniaturized PDID, respectively. In yet another non-limiting example, any detector herein is miniaturized to include a microstructure. For instance, the detector has a dimension be between about 20 μm to 1 mm.

Despite extreme miniaturization, our miniPDID's un-optimized performance was 3-fold lower in sensitivity compared to a commercial mini-unit. With optimization of gas flow rate, voltage bias, and GC outlet position, this gap will be bridged and perhaps sensitivity improved. The detector was rugged, as evidenced by near continuous operation for nine months without a single failure. Additional details follow.

PDID Detector

The PDID detector includes a core having components to produce a plasma discharge capable of photoionizing an analyte and to detect any resultant electrons, thereby identifying the analyte by its unique electronic or current signature. In some embodiments, the core includes one or more electrodes, insulators, and/or positioners (e.g., any described herein).

Figure 1A:
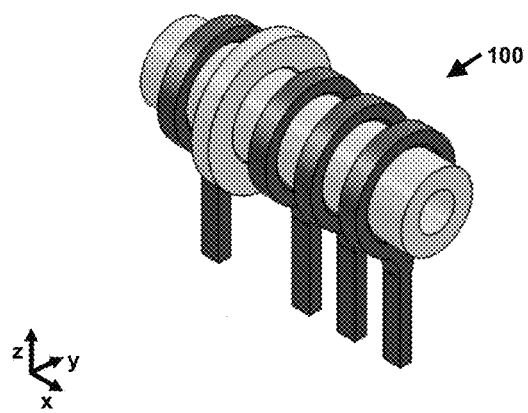
FIG. 1A-1H provides schematics of an exemplary PDID core 100, which includes at least one electrode 110 and one insulator 120. Provided are schematics in FIG. 1A which is a perspective view, FIG. 1B which is an exploded view, FIG. 1C which is an end view, FIG. 1D which is a cross-sectional view, and FIG. 1E which is a side view. Also provided are schematics of the core in use, including FIG. 1F which is a cross-sectional view of the core before plasma discharge.
Figure 1B:
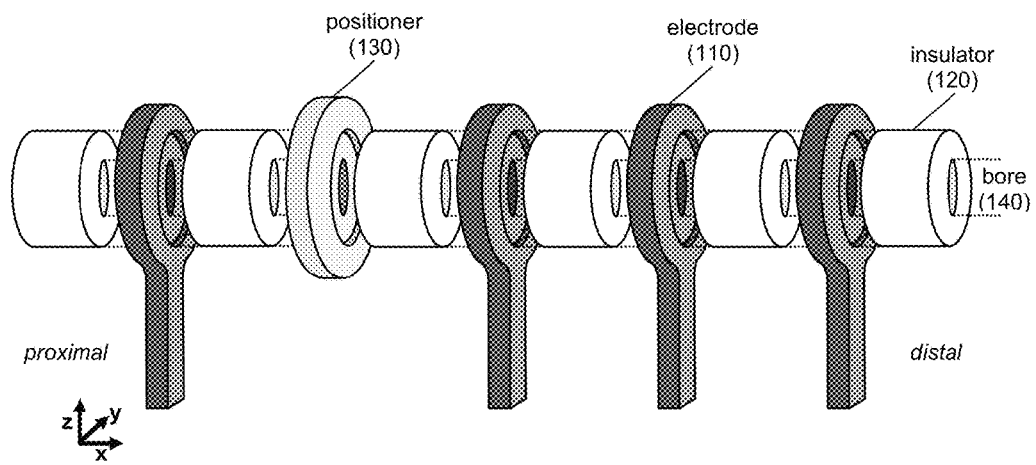

An exemplary schematic of the core, as well as its use, is provided in FIG. 1A-1H. As shown in FIG. 1A-1B, the core 100 can include a plurality of electrodes 110 and insulators 120, where the electrodes and insulators are placed alternately. In particular embodiments, each of the electrodes and insulators have a proximal face and a distal face.

The electrodes 110 and insulators 120 are configured to provide a bore 140 that extends through the core, thereby defining the chamber 106 of the core (FIG. 1B-1E). In particular embodiments, each of the electrodes and insulators has an annular configuration.

Figures 1C, 1D:
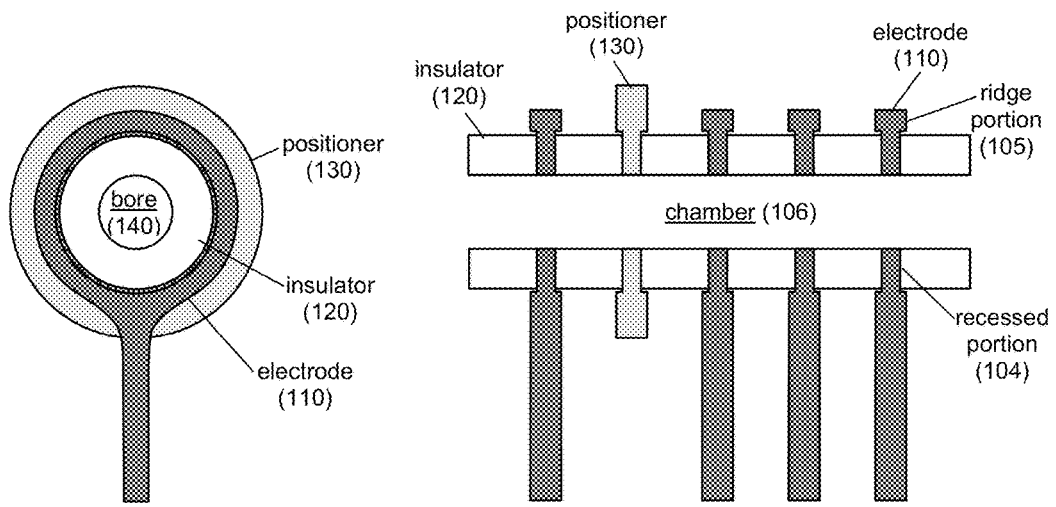
Figure 1E:
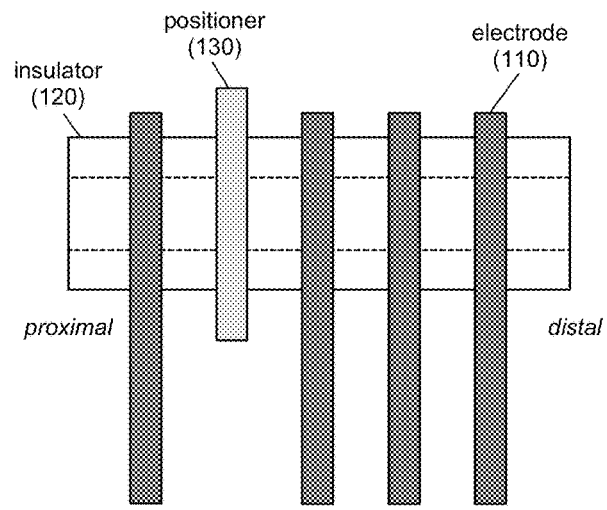

As shown in FIGS. 1B and 1D, the electrodes 110 and insulators 120 are configured to nest within each other. In one embodiment, at least one of the proximal and distal faces of the electrode is configured to provide a recessed portion 104 and/or a ridge portion 105. In another embodiment, at least one of the proximal and distal faces of the insulator is configured to nest within the recessed portion of the electrode and/or contact a surface of the ridge portion. In yet another embodiment, each of the recessed and ridge portions has an annular configuration, e.g., disposed around the bore.

Optionally, the core can include a positioner 130, e.g., formed from an insulating material, to aid in aligning and compressing the assembly to form the core. The positioner can include, e.g., a recessed portion on each of its proximal and distal faces. FIG. 7A-7D provides an exemplary schematic of a positioner with non-limiting dimensions for the bore, ridge portion, and recessed portion.

In use, the core can be used for any useful detection mode, including a pulsed discharge helium ionization detector (PDHID) mode, a pulsed discharge electron capture detector (PDECD) mode, and a pulsed discharge emission detector (PDED) mode.

Figure 1F:
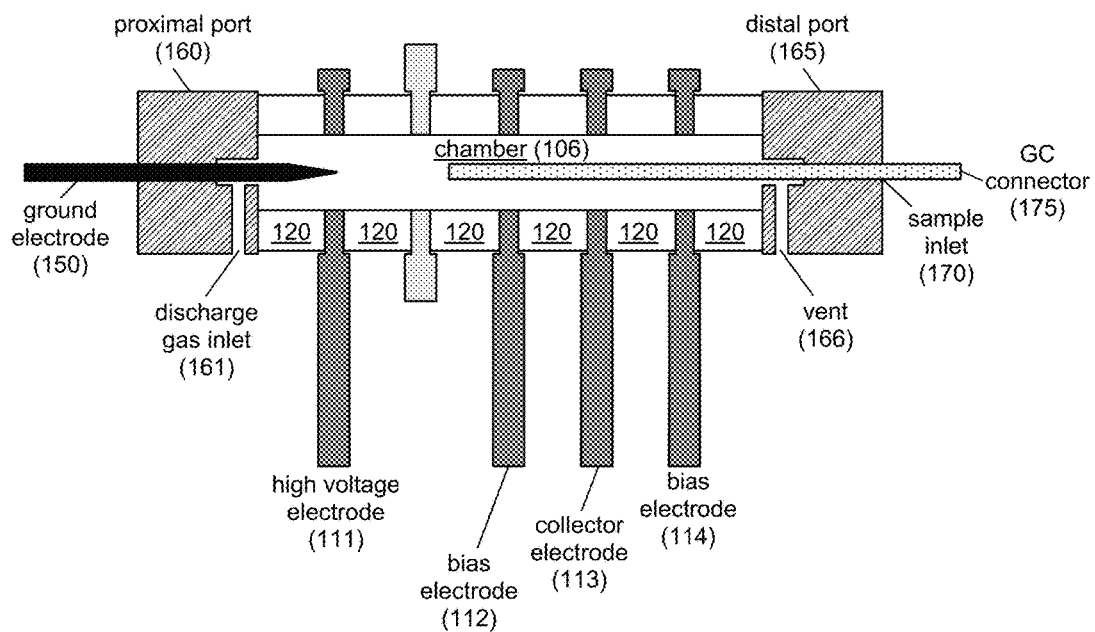
Figure 1G:
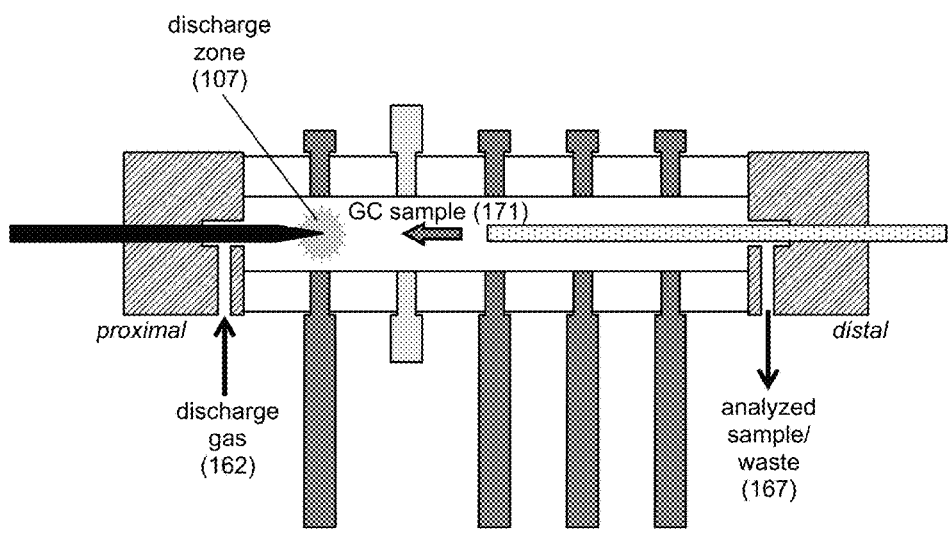

FIG. 1F-1G shows an exemplary use in PDHID mode. In PDHID mode, the detector uses a plasma discharge to photoionize analytes eluting from a GC column. To minimize contamination of the plasma discharge source, a discharge gas is usually pumped into the core, where the flow of this discharge gas is counter to the flow of the GC eluents (e.g., analytes). An exemplary core includes a high voltage electrode 111, a bias electrode 112, a collector electrode, and another bias electrode 114. These electrodes are positioned alternately with annular insulators 120. The bore of the insulators and electrodes, once aligned, defines the chamber 106.

The core can be capped by ports, such as a proximal port 160 and a distal port 165. The proximal port 160 includes one or more inlets and outlets configured to provide the ground electrode 150 and/or a discharge gas inlet 161. The distal port 165 includes one or more structures configured to deliver the GC eluent or analyte into the core, where these structures can include a sample inlet 170 (e.g., configured for fluidic communication between a GC connector 175 and the chamber 106) and a vent 166 (e.g., configured for fluidic communication between the chamber 106 and a storage container). FIGS. 8A-8C and 9A-9C provide exemplary schematics for ports having inlets and outlets.

As shown in FIG. 1G, the PDHID mode can be implemented by using the ground electrode 150 and the high voltage (HV) electrode 111 to create a discharge zone 107. The discharge gas 162 can be any useful gas. In one embodiment, the discharge gas 162 is pure helium (e.g., $He_2$), thereby providing a discharge zone 107 including photon emissions from a transition of diatomic helium ($He_2$) to the dissociated helium ground state (2 He). These Hopfield emissions photoionize the analyte (e.g., the GC sample 171), which produces electrons that are focused toward the collector electrode 113 by the twin bias electrodes 112, 114. These electrons, arising from interactions with the analyte, can produce an electronic signature, which is detected as a change in current. In particular embodiments, the flow of the discharge gas 162 is counter to the flow of the analyte 171 (e.g., the GC sample).

After analysis, the analyzed sample or analyte 167 can be collected through the vent 166. These analyzed samples can be collected and stored for later analysis and/or confirmation, e.g., by using any useful storage container (e.g., as described in Manginell R P et al., "A materials investigation of a phase-change micro-valve for greenhouse gas collection and other potential applications," *Rev. Sci. Instrum.* 2012; 83:031301 (11 pp.), which is incorporated herein by reference in its entirety).

Figure 1H:
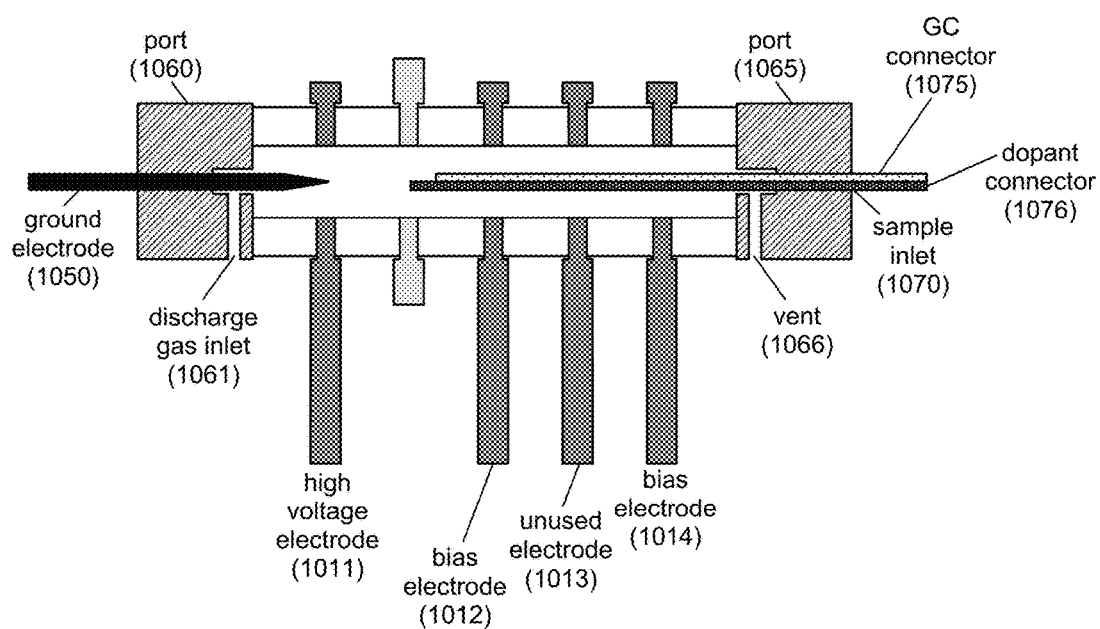

FIG. 1H shows an exemplary use in a PDECD mode. In this mode, a dopant is injected into the PDID core, where this dopant provides thermalized electrons upon being photoionized by the Hopfield emission. For instance, the dopant, e.g., a dopant gas, is introduced into the chamber and ionized in the discharge zone. The photoionized dopant provides thermalized electrons that interact with the analyte. Whereas the photoionized dopants provide a standing current, interactions of the analyte with the dopant's thermalized electrons and/or the Hopfield emission produce an electronic signature, which is detected as a change in the standing current.

As shown in FIG. 1H, the PDECD mode can be implemented by using a ground electrode 1050 and a HV electrode 1011 to create a discharge zone. The core also includes a bias electrode 1012 and another bias electrode 1014, where one electrode is connected to an electrometer and the other is configured to provide bias. If the same design is to be employed for both PDHID and PDECD, then the collector electrode in PDHID can be the unused electrode 1013 for PDECD. Optionally, the core can also be aligned to omit unused electrodes.

The core can be capped by a proximal port 1060 and a distal port 1065. The proximal port 1060 includes one or more inlets and outlets configured to provide the ground electrode 1050 and/or a discharge gas inlet 1061. The distal port 1065 includes one or more structures configured to deliver the dopant and GC eluent or analyte into the core, where these structures can include a sample inlet 1070 (e.g., configured for fluidic communication between a GC connector 1075, a dopant connector 1076, and the chamber) and a vent 1066 (e.g., configured for fluidic communication between the chamber and a storage container). Optionally, the distal port 1065 can include a dopant inlet separate from the sample inlet 1070, where the dopant inlet is configured for fluidic communication between a dopant connector 1076 and the chamber. In particular embodiments, the dopant is introduced closer to the discharge zone than the analyte or sample. The dopant can include any useful dopant, such as argon (Ar), krypton (Kr), hydrogen (e.g., $H_2$), $CO_2$, $NH_3$, $N(CH_3)_3$, $CH_4$, nitrogen (e.g., $N_2$), or xenon (Xe) in any useful amount.

In particular embodiments, the flow of the discharge gas and the analyte (e.g., analyte gas or GC eluent) are generally counter to one another, with the advantage that if the discharge gas flow is greater than the analyte flow, the analyte never reaches the low- and high-voltage electrodes. This reduces degradation and contamination of the electrodes, which is a constant problem in other non-radioactive ionization approaches that have been described in the literature. These issues lead to high maintenance costs and unreliability in non-radioactive ionization sources.

Figure 3:
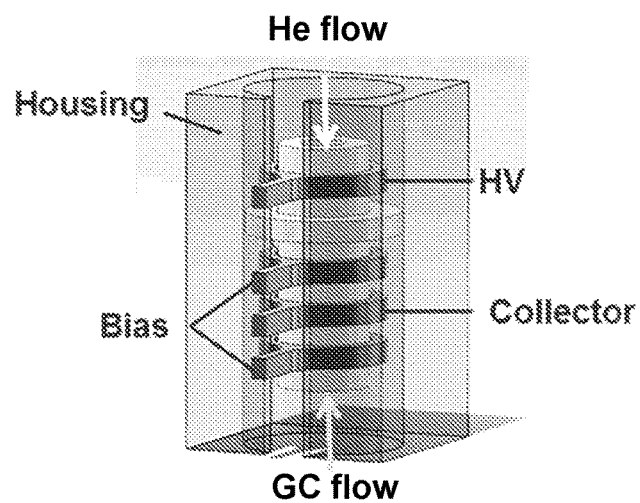
FIG. 3 is a solid model of an exemplary PDID core. The block-shaped external housing is electrically grounded for safety and is shown semi-transparent to allow the core of the detector to be seen. The white ceramic insulators and gray electrodes are both annular and the internal diameter of these forms the central flow channel of the detector. The tangs protruding from the annular electrodes insert into spring contacts in the ceramic circuit board shown in FIG. 11B-11C. The central flow channel of this baseline design is 3 mm ID by 17.5 mm long.

An exemplary core having the housing is shown in FIG. 3. The block-shaped external housing was electrically grounded for safety and is shown semi-transparent to allow the core of the detector. The white ceramic insulators and gray electrodes are both annular, and the internal bore of these forms the central flow channel of the detector. In one non-limiting example, the central flow channel of this baseline design has an internal diameter of about 3 mm and a length of about 17.5 mm.

This unique electrode design allowed for nesting of the insulators, so that the overall core of the detector can be self-aligned and compressed together in assembly. This method of manufacture allows for close spacing of the electrodes for miniaturization and robust, inexpensive manufacture. The tangs protruding from the annular electrodes are inserted into spring contacts (e.g., Mill-Max model 0342) in the ceramic circuit board.

Figure 10A:
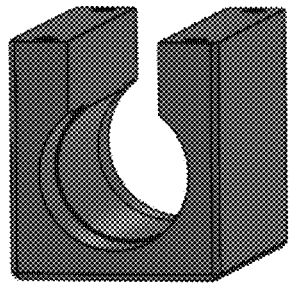
FIG. 10A-10B provides schematics of an exemplary housing in (A) perspective view and (B) cross-sectional view. All measurements are provided in mm, unless otherwise indicated.
Figure 10B:
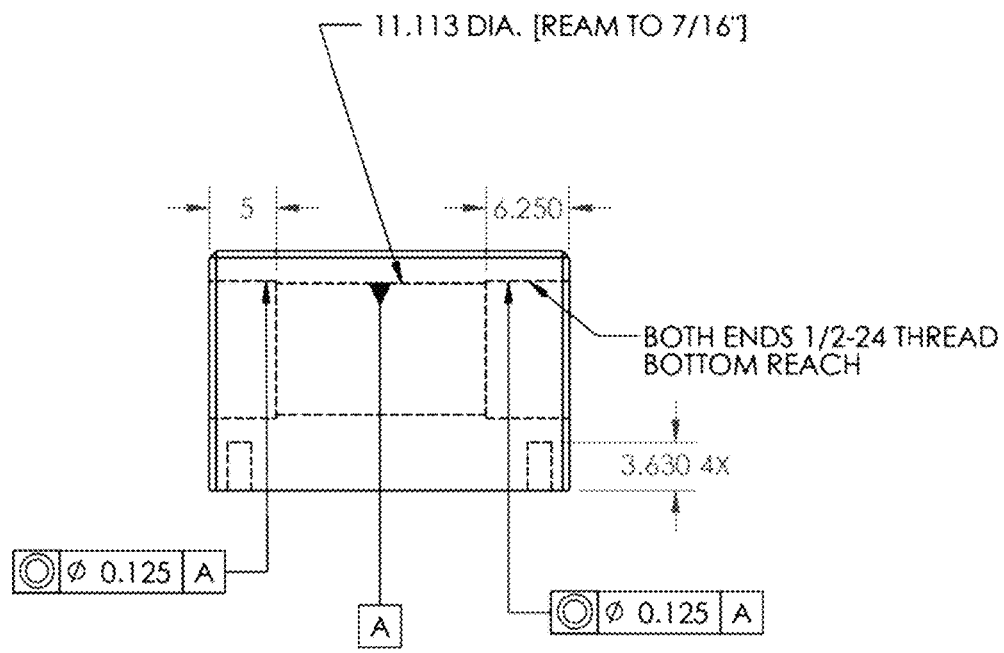

In some embodiments, the electrodes and/or housing are formed from stainless steel for relative chemical inertness. The stainless could be passivated further through a variety of commercial processes, such as the Silco Steel® method of, e.g., depositing an amorphous silicon coating on a steel surface, as described in U.S. Pat. No. 6,444,326, which is incorporated herein by reference in its entirety. The electrode designs were rapid prototyped from stainless steel using photochemical etching at Vacco, Inc. FIG. 10A-10B provides an exemplary schematic of a housing.

In some embodiments, the insulators are machined annular ceramic (99.6% alumina) insulators, which, together with the dark gray annular electrodes, create the central flow channel. In other embodiments, the insulators are chemically inert and electrically isolate the bias, signal, and HV electrodes from one another.

Figure 4A:
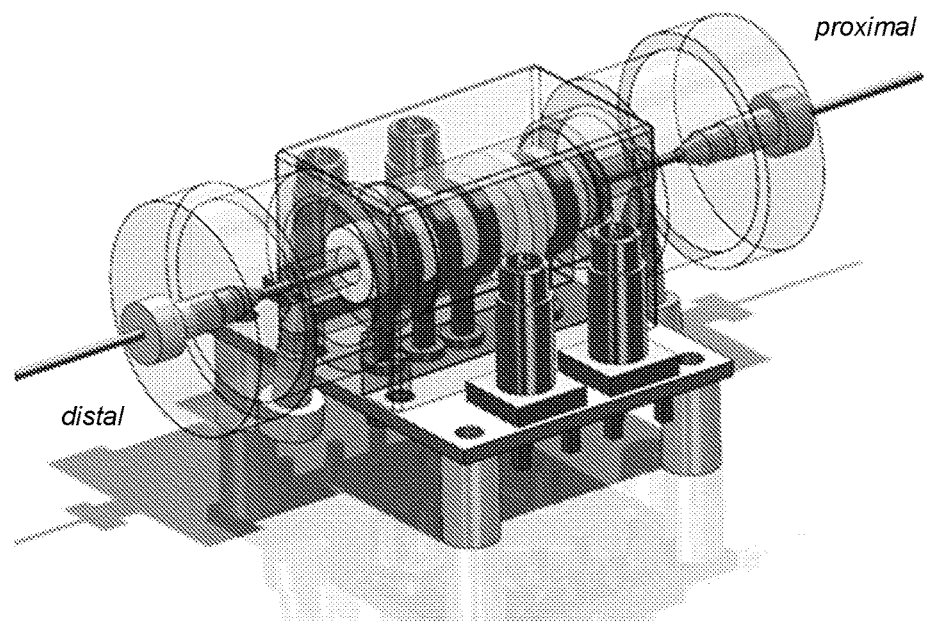
FIG. 4A-4B provides FIG. 4A which is a solid model.
Figure 4B:
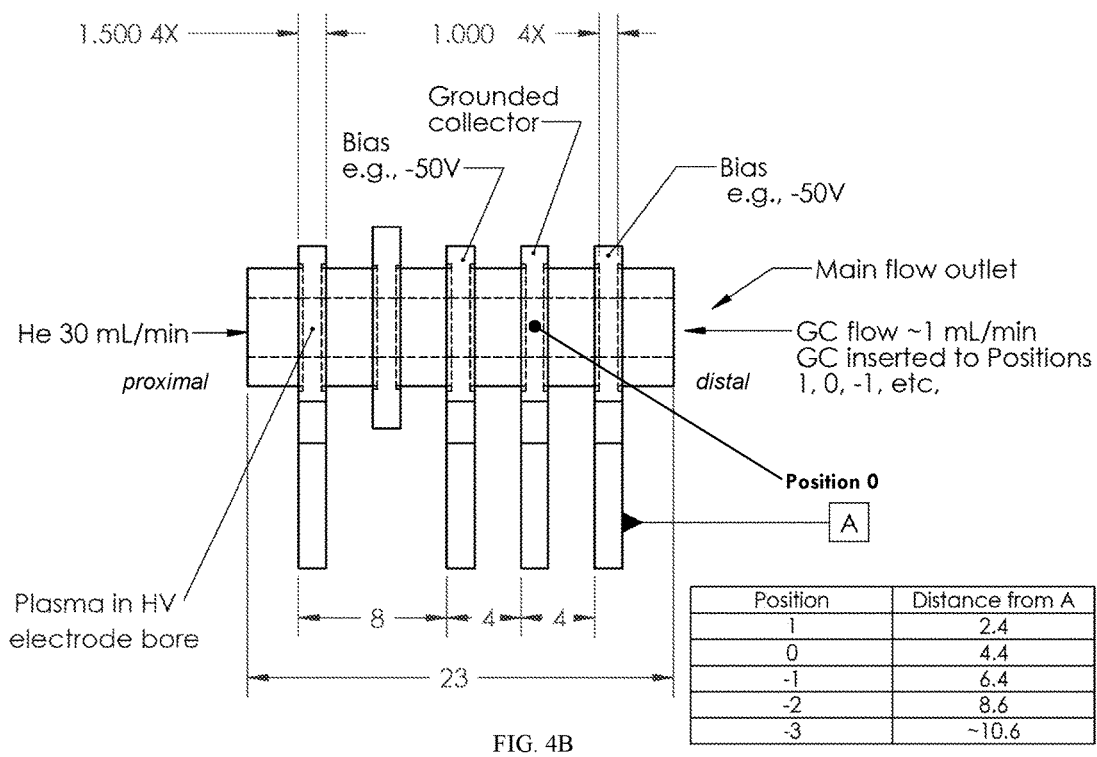
Figure 5C:
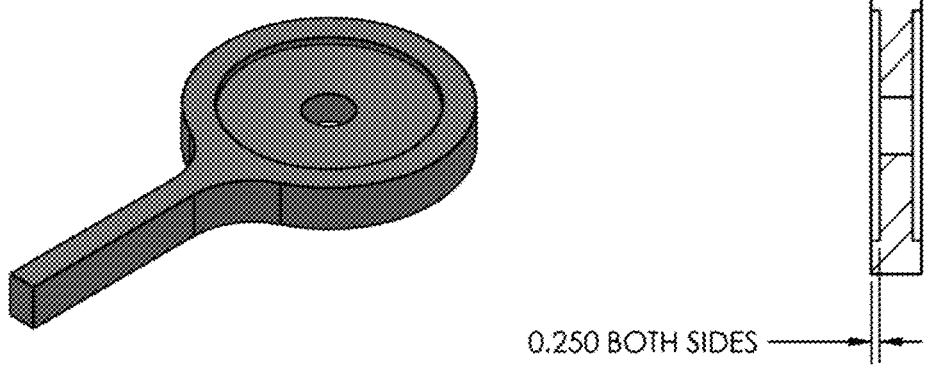
Figure 5C:
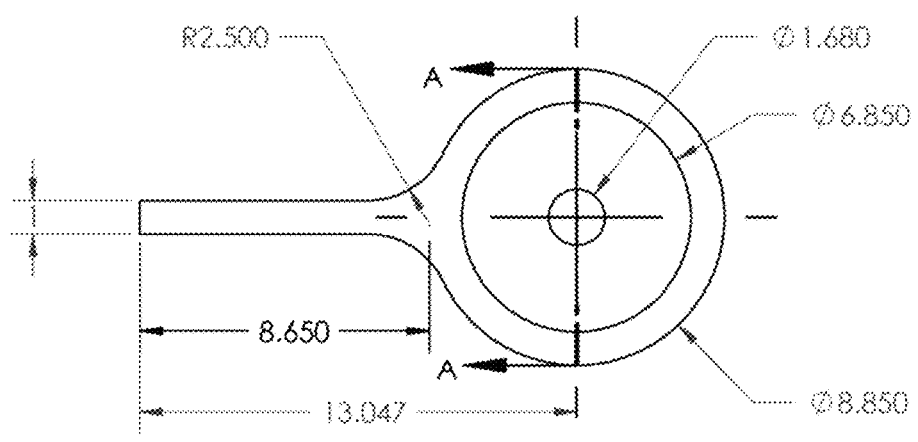
Figure 5D:
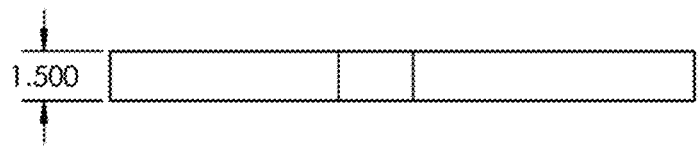
Figure 7A:
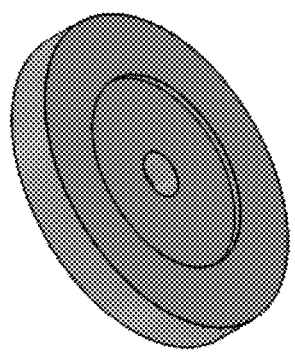
FIG. 7A-7D provides schematics of an exemplary positioner in (A) perspective view, (B) cross-sectional view, along sectional line B-B in FIG. 7D, (C) cross-sectional view, along sectional line C-C in FIG. 7D, and (D) plan view. All measurements are provided in mm, unless otherwise indicated.
Figure 7B:
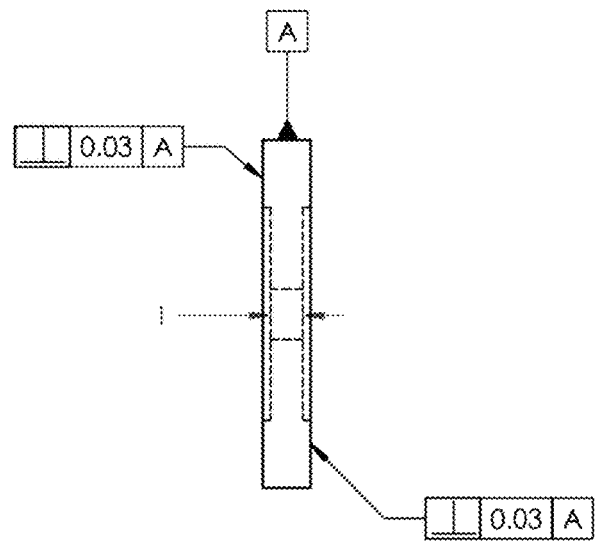
Figure 7C:
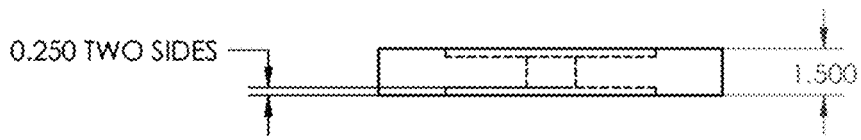
Figure 7D:
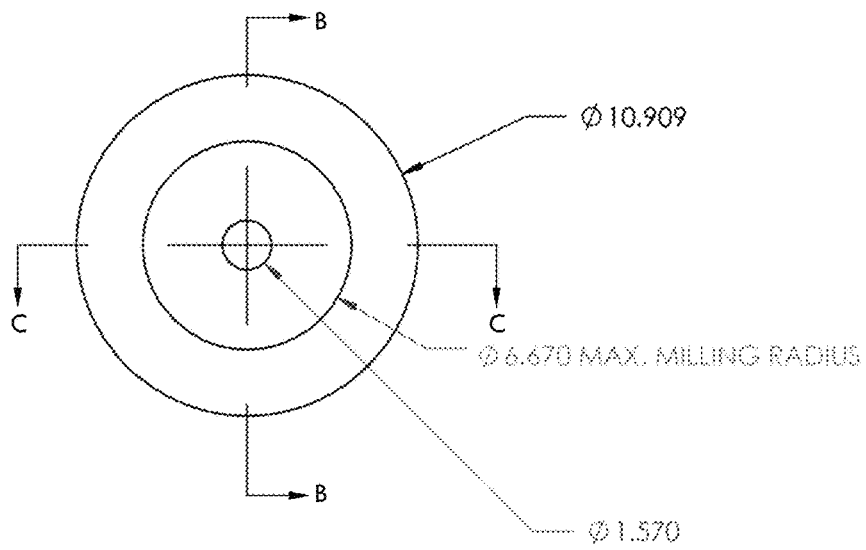
Figure 8A:
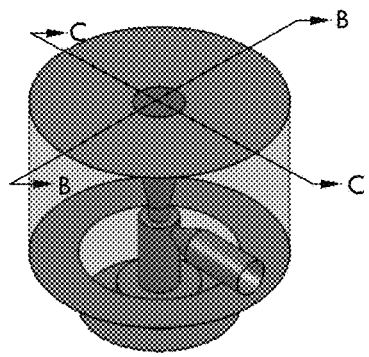
FIG. 8A provides schematics of an exemplary port in a perspective view.
Figure 8B:
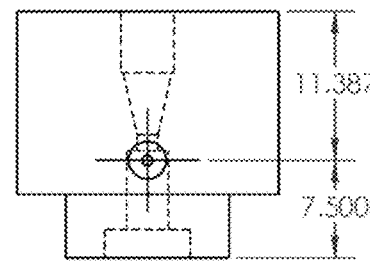
FIG. 8B provides schematics of an exemplary port in a cross-sectional view.
Figure 8C:
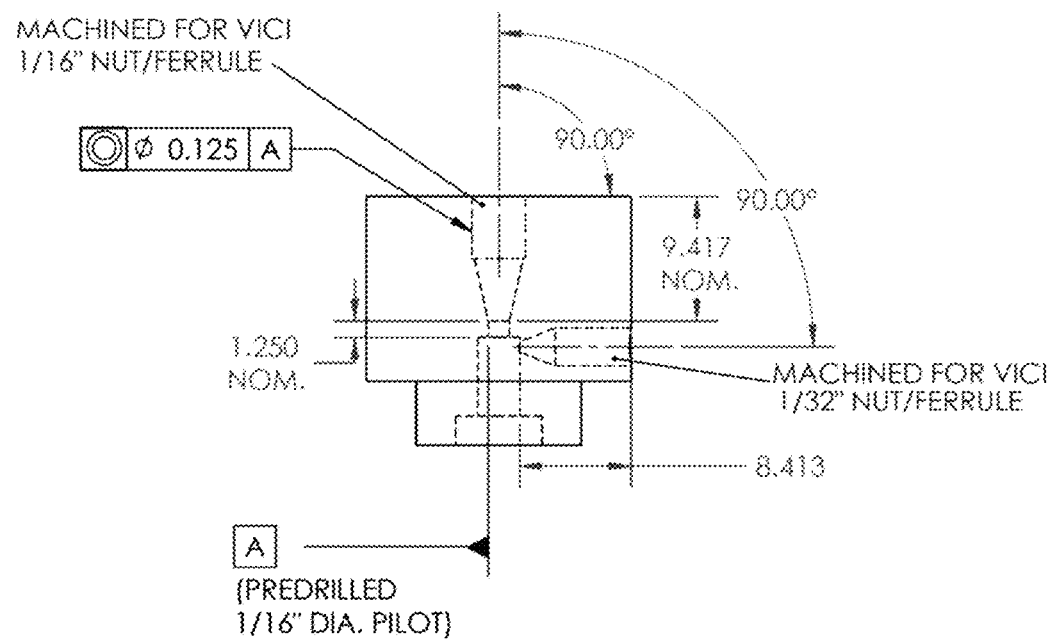
FIG. 8C provides schematics of an exemplary port in a cross-sectional view.
Figure 9A:
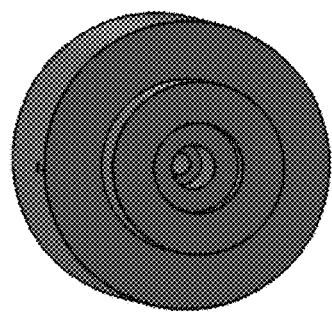
FIG. 9A-9C provides schematics of another exemplary port in (A) bottom view, (B) perspective view, and (C) cross-sectional view. All measurements are provided in mm, unless otherwise indicated.
Figure 9B:
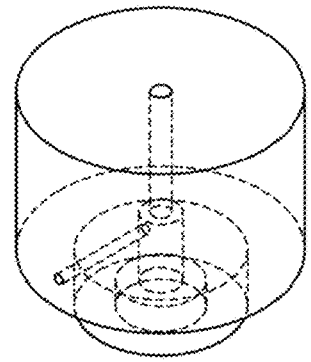
Figure 9C:
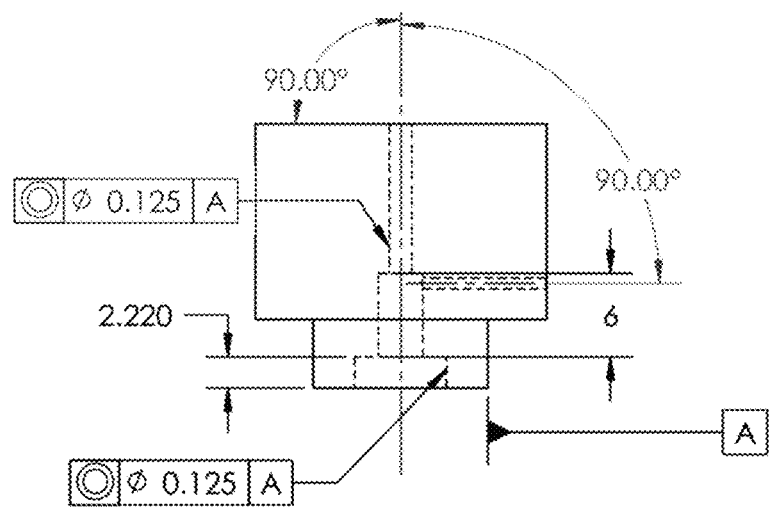

FIG. 4A-4B provides additional details of an exemplary detector, including a housing surrounding the core, a circuit board connected to the electrodes, and proximal and distal ports. In particular, FIG. 4B provides a schematic of the core, which includes a HV electrode, a positioner, a bias electrode, a grounded collector electrode, and another bias electrode (from left to right) with insulators dispersed between these elements. Exemplary He discharge gas flow rates, GC sample flow rates, bias voltages, and detector dimensions are provided.

Electrodes and Insulators

The electrodes of the application were designed to simplify interconnection of the detector with standard circuit boards using standard circuit board connectors. The circuit board can provide either a direct interconnection or an indirect interconnection to electronics. For a direct interconnection, the electrode can interface directly with the circuit board, which includes control and sensing electronics. This option would enable manufacturable methods of miniaturization, thereby ultimately providing a detector size that is significantly smaller than conventional PDID designs in which separate, cable-connected, electronics subsystem is used. The ability to place the electronic measurement adjacent to the collector may also have advantages in signal-to-noise performance. Alternatively, for an indirect interconnection, the electrode is connected to the circuit board, which in turn routes control and sensing lines to a multitude of electrical connectors, including commercial ultra-miniature board connectors (e.g., those from Positronic Industries, Inc.).

Figure 2A:
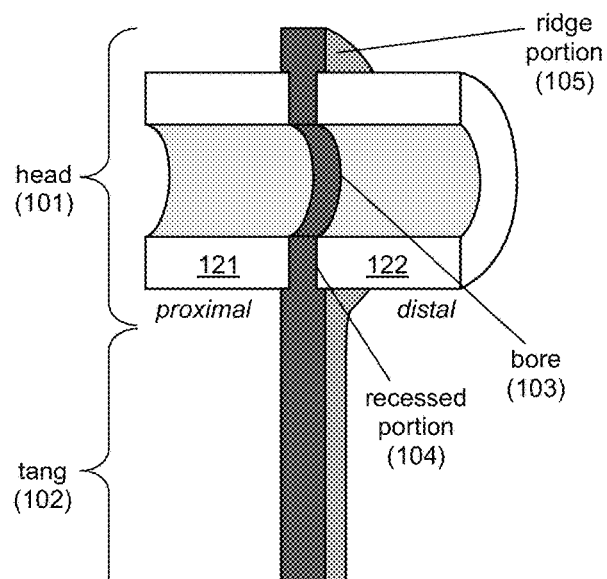
FIG. 2A provides schematics of the proximal and distal faces of an exemplary electrode 115 and insulators 121, 122.

Exemplary electrodes are provided in FIG. 2A. As can be seen, the electrode 115 includes a head 101 and a tang 102. The head 101 includes structures configured to interconnect with the insulator(s), as well as a bore that aligns with bore(s) in insulator(s) to form the chamber of the PDID core. The tang 102 includes structures configured to interconnect with a circuit board, e.g., an elongated structure configured to be inserted into a circuit board.

The electrodes and insulators can have any useful geometry (e.g., circular, annular, semi-circular, rectangular, square, etc. for the recessed portion, bore, ridge portion, electrode face, electrode head, electrode tang, and/or insulator face) or dimension (e.g., any described herein). Exemplary dimensions include those in FIG. 2B, such as electrode length along the x-direction $e_{length}$, electrode bore length along the x-direction $e_{b,length}$, electrode head height along the z-direction $e_{h,height}$, electrode tang height along the z-direction $e_{t,height}$, electrode ridge length along the x-direction $e_{r,length}$, electrode ridge height along the x-direction $e_{r,height}$, bore height along the z-axis for either the electrode and/or insulator $b_{height}$, insulator length along the x-direction $i_{length}$, and insulator height along the z-direction $i_{height}$. Any of these dimensions can be of from about 10 μm to about 1 mm.

Figure 2B:
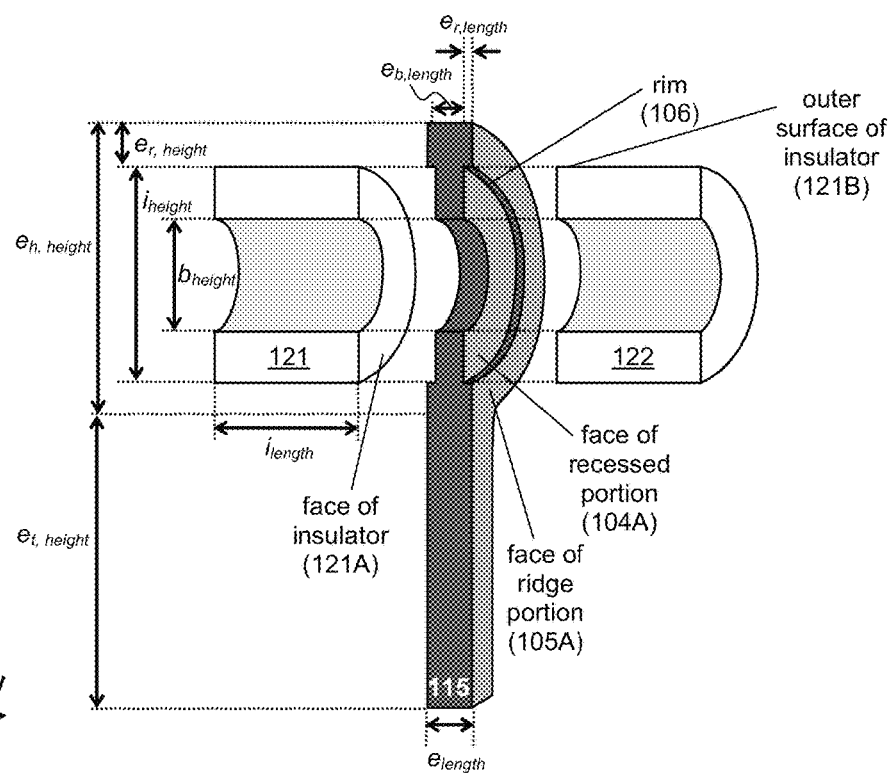
FIG. 2B provides schematics of the proximal and distal faces of an exemplary electrode 115 and insulators 121, 122.

In one embodiment, as shown in FIG. 2B, the head portion 101 includes a bore 103, a recessed portion 104 surrounding the bore, and a ridge portion 105 surrounding the recessed portion. In another embodiment, the bore 103 of the electrode is configured to align with the bore of adjacent insulators 121, 122. In some embodiments, each bore of the electrode(s) and insulator(s) has the same bore height $b_{height}$.

In yet another embodiment, each of the proximal and distal faces of the electrode 115 includes a recessed portion 104, where each of the recessed portions 104 is configured to receive at least one face of the insulators 121, 122. For instance, a dimension of the recessed portion (e.g., $e_{r,height}-(2 \times e_{r,height})$) is about the same or slightly larger (e.g. have a tolerance that is about 1%, 2%, 3%, 4%, or 5% of the dimension of the recessed portion) than a dimension of the insulator face (e.g., $i_{height}$). In another instance, a geometry of the recessed portion is the same a geometry of the insulator face (e.g., both the recessed portion and the insulator includes a circular or annular face). In yet another instance, the face of the recessed portion 104A is conformal to the face of the insulator 121A.

In one embodiment, each of the proximal and distal faces of the electrode 115 includes a ridge portion 105, where each of the ridge portions 105 is configured to circumscribe the edge of at least one face of the insulators 121, 122. For instance, a dimension or surface of the ridge portion contacts a surface or edge of the insulator. For example, the surface of the ridge portion includes a surface along a rim 106 of the ridge portion (e.g., along dimension $e_{r,length}$), where the rim 106 is the surface disposed between a face of the recessed portion 104A and the face of the ridge portion 105A and where the surface of the rim is in a plane that is orthogonal to the planes of the faces of the recessed and ridge portions. In some embodiments, the rim is a surface in the x-plane, e.g., a surface disposed along dimension $e_{r,length}$. In another instance, the electrode ridge length $e_{r,length}$ is dimensioned to provide a conformal contact with an edge or a surface of the insulator (e.g., the outer surface of the insulator 121B).

Figures 11A, 11B, 11C:
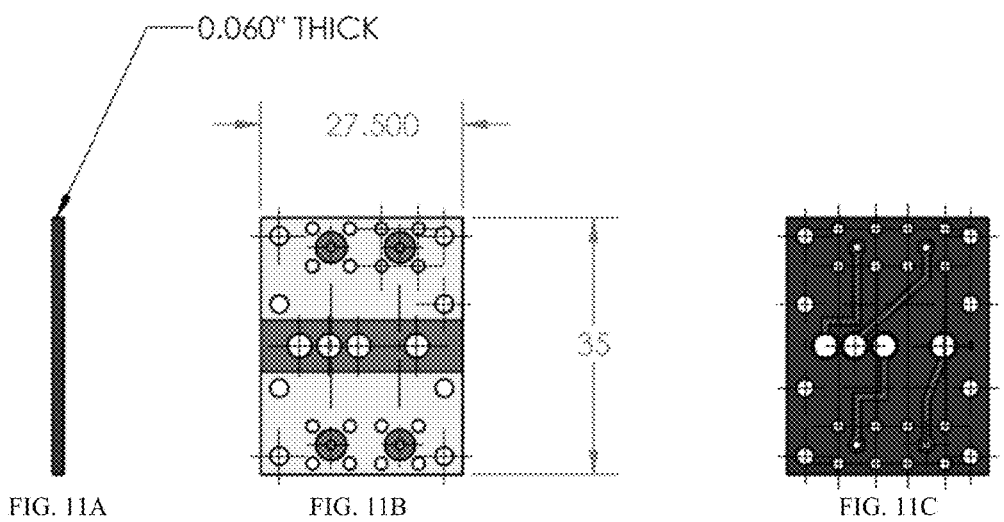
FIG. 11A-11C provides schematic of an exemplary circuit in (A) side view, (B) top view, and (C) bottom view. All measurements are provided in mm, unless otherwise indicated.

Dimensions are provided for exemplary electrodes, insulators, and circuit boards. For instance, FIG. 5A-5D provides an exemplary schematic of an electrode with non-limiting dimensions for the bore, tang, head, ridge portion, and recessed portion. In particular embodiments, $b_{height}$ is any useful dimension, such as a diameter of about 1 mm, 1.5 mm, 2 mm, or 3 mm. FIG. 6A-6C provides an exemplary schematic of an insulator with non-limiting dimensions for the bore, height, and length (e.g., $b_{height}$, $i_{length}$, or $i_{height}$). FIG. 11A-11C provides an exemplary schematic of a circuit board (e.g., to be employed with any electrode (e.g., FIG. 5A-5D), insulator (e.g., FIG. 6A-6C), or assembly (e.g., in FIGS. 3 and 4A-4B).

The electrodes and insulators of this application can be manufactured by any useful method, such as rapid prototyping techniques (photo-chemical etching), laser machining, and/or standard machining methods. The tang of the electrode allows for easy interconnection to circuit boards, as mentioned above. The electrode and insulator design also allows for nesting of the inter-electrode insulators for alignment and assembly. The PDID components can be formed from any useful material, such as a conductive material for the electrode (e.g., stainless steel, or any other material described herein) and an insulative material for the insulator (e.g., alumina, or any other material described herein).

The electrodes and insulators can be modified to obtain a detector having any useful dimension and/or parameter. For instance, the central hole or bore diameter $b_{height}$ of the electrode and insulator helps define the internal volume of the detector, and can be easily modified in the manufacturing process. In another instance, the axial extent of the detector (e.g., along the x-axis) is the other contributing dimension to the internal volume. The axial extent of the detector is determined by the electrode bore length $e_{b,length}$ and insulator length $i_{length}$, where these dimensions are shown in FIG. 2B. Each of these dimensions is easily modified, unlike conventional PDID manufacturing methods.

The electrodes can have any useful purpose. For instance, exemplary electrodes include collector electrodes, bias electrodes, ground electrodes, high voltage electrodes, low voltage electrodes, field-confinement electrodes, and field-shaping electrodes.

The detector can have any useful number of electrodes (e.g., annular electrodes) and insulators (e.g., annular insulators). In one embodiment, the detector includes n electrodes and n+x insulators, where n is an integer selected from 1 to 10 and x is an integer selected from 0 to 10. In one particular embodiment, one of the n electrodes is a ground pin electrode. In some embodiments, the detector includes n electrodes, m positioners, and m+n+1 insulators, where each of n and m is, independently, an integer selected from 1 to 10. In other embodiments, the detector includes n electrodes and n+1 insulators, where n is an integer selected from 1 to 10. In yet other embodiments, the detector includes a plurality of electrodes and a plurality of insulators, where each electrode is disposed between two insulators.

In one embodiment, the PDID detector has a minimal set of four electrodes, which includes a high voltage electrode, a ground electrode, a bias electrode, and a collector electrode (e.g., connected electrically to an electrometer). In a further embodiment, each of the high voltage electrode, bias electrode, and collector electrode is an annular electrode, and the ground electrode is a pin electrode. In another embodiment, the PDID detector includes five electrodes, which includes a high voltage electrode, a ground electrode, two bias electrodes, and a collector electrode (e.g., connected electrically to an electrometer). In yet another embodiment, each of the high voltage electrode, bias electrodes, and collector electrode is an annular electrode, and the ground electrode is a pin electrode. In a further embodiment, the PDID detector includes any other additional electrode, e.g., a field-shaping electrode.

Ionization Source

The detector of the application can have any useful ionization source. In one embodiment, the ionization source is a non-radiation ionization source. An exemplary non-radiation ionization source is provided in FIG. 1F-1G. As can be seen in FIG. 1F, the non-radiation ionization source includes a ground electrode 150, a high voltage electrode 111, and optionally a discharge gas inlet 161. In one embodiment, the ground electrode 150 is a pin electrode having a distal portion disposed within a bore of an annular high voltage electrode 111. Optionally, the ground electrode is replaced with a low voltage electrode. This design is also amenable to miniaturization and portable use allowing elimination of the storage and transportation issues that arise with radioactive sources.

As seen in FIG. 1F, the discharge gas inlet 161 is configured to introduce a discharge gas into the chamber 160 of the detector core. The discharge gas inlet can introduce any useful discharge gas, e.g., a plasma gas, including helium (e.g., $He_2$), argon (Ar), krypton (Kr), hydrogen (e.g., $H_2$), $CO_2$, $NH_3$, $N(CH_3)_3$, $CH_4$, nitrogen (e.g., $N_2$), or xenon (Xe); or an excimer gas (e.g., $F_2$, $Ar_2$, $Kr_2$, $Xe_2$, ArF, ArCl, ArBr, KrF, KrCl, XeBr, XeCl, or XeF), as well as mixtures thereof.

In use, an external control circuit is used to create a direct current (DC), pulsed DC, AC (alternating current), or radio-frequency (RF) discharge across the gap between the two electrodes, which are bathed in the discharge gas. Typically, the discharge gas is flowing from the inlet. But discharge gas might be introduced discontinuously (e.g., in a pulsed manner).

The combination of the discharge and the discharge gas creates a discharge zone including a plasma. The plasma excitation and de-excitation processes create infrared, visible, and ultraviolet (UV) photons. The plasma photons travel down the bore of the core, where they interact with analytes or the sample introduced at the opposite end of the bore. Such analytes are generally photo-ionized; however, reactive-charged species from the plasma can also propagate sufficiently far to generate ionization events. Reactive gases, such as methylene chloride, could also be introduced with analytes to promote electron transfer reactions. This discharge zone, in turn, is located upstream of a detection zone (e.g., a chamber of a detector).

The ionized analytes can be detected electronically via additional electrodes, such as by using any detector described herein. Generally, the flow of the discharge gas and the sample gas (containing an analyte) are generally counter to one another, with the advantage that if the plasma flow is greater than the sample flow, then the analyte never reach the ground, low-voltage, and/or high-voltage electrodes. This reduces degradation and contamination of the electrodes, which is a constant problem in other non-radioactive ionization approaches. These issues lead to high maintenance costs and unreliability in nonradioactive ionization sources.

This source can be used in the macroscale, but also has the advantage of being miniaturizeable, size-scalable, and manufacturable. Furthermore, electronic gating, e.g., on millisecond time scale, of the plasma source is possible. Gating, in turn, allows for gated ionization by the mechanisms mentioned above (photo-ionization, transfer reactions, etc.). Therefore, the present application can be used to replace the radioactive source and ion gates of IMS and similar instruments to eliminate ion gates for IMS and other instruments, as well as to facilitate correlation ion mobility spectrometry.

Accordingly, in some embodiments, the non-radioactive ionization source can include a gate (e.g., located between the discharge zone and the detection zone). The gate can include, e.g., a potential capture well (e.g., configured to control the injection of ions into the detection zone), a shutter (e.g., an electrostatic ion shutter, such as a Bradbury-Nielson or Tyndall type shutter), and/or a set of gates (e.g., an entrance gate and an exit gate). The gate can be controlled by employing a gate drive circuit that provides a gating function (e.g., a binary modulation, an analog modulation, or a Fourier transform approach) and/or a trigger signal. Additional components and are described in U.S. Pat. No. 7,417,222, which is incorporated herein by reference in its entirety.

In particular embodiments, the gate (e.g., an ion shutter) is controlled or modulated by a gating function, which in turn includes a binary modulation (e.g., a Barker code) or an analog modulation (e.g., a chirped sinusoid). In some embodiments, a Barker code is employed, where this code is a binary coding pattern of finite length (e.g., 2 or more, such as of from about 2 to 13) that has an autocorrelation with equal and low sidelobes. A non-radioactive ionization source with a Barker code (e.g., a 13-bit Barker code) could be employed to average the information content of a plurality of measurement cycles (e.g., ten or more cycles) into one correlation sample interval, thereby providing greater signal fidelity in a much reduced time interval, as well as signal-to-noise enhancement.

The gating function can be implemented in any useful manner. For example, a series of sample injections can be made to the PDID detector, and continuous data can be collected using a digital audio tape recorder (DAT). The DAT can then be interfaced by a direct connection to a built-in analog interface, which can further include the raw detector output and the gate trigger. A gate drive circuit can be constructed, based on a programmable integrated controller, to generate a Barker pattern, and inserted in series between the interface and the spectrometer gate. In this modality, the gate drive circuit receives the gate trigger from the interface and in-turn provides a modulation pattern that is applied to the gate with minimal delay.

In particular, when the detector is employed to provide a correlation mobility spectrum, the system can further includes a filter (e.g., a matched filter) configured to correlate the ion response signal (e.g., from the detector) with the ion current modulation (e.g., from a gate or gating function) to provide a correlation mobility spectrum.

Another important advance is the control of the ionization energy in the analytical instrument. Current radioactive sources produce ions at fixed energies that can interfere with the desired detection by breaking the chemical bonds of some complex organic molecules and causing chemistry in the analytical instrument that disguises or disrupts the detection of the analyte of interest. The ability to control the energy and power of the ionization source will allow for tuning of the ionization energy and add an additional dimension to the detection method. The non-radioactive ionization source can be employed with any detector, such as a mass spectrometer (MS), an ion mobility spectrometer (IMS) (e.g., such as those in U.S. Pat. Nos. 7,155,812 and 7,417,222, each of which is incorporated herein by reference in its entirety), an electron capture detector (ECD), and/or a PDID. The target analytes that are ionized by this source can be detected electronically via additional electrodes (e.g., as in the PDID) or further manipulated (e.g., as in the IMS or MS) using fluid flow or electric and magnetic fields.

System

The present application also includes a detector (e.g., any described herein) connected to any other useful structure or component. Exemplary components include a circuit board, a storage container (e.g., any container herein, such as that described in Manginell R P et al., "A materials investigation of a phase-change micro-valve for greenhouse gas collection and other potential applications," *Rev. Sci. Instrum.* 2012; 83:031301 (11 pp.), which is incorporated herein by reference in its entirety, that is in fluidic connection with a vent of the detector); valves, such as those in Galambos P et al., "Active MEMS valves for flow control in a high-pressure micro-gas-analyzer," *J. Microelectromech. Sys.* 2011 October; 20(5):1150-62, which is incorporated herein by reference in its entirety; a pulsed train system; a microGC system (e.g., in fluidic connection with a chamber of the detector by way of the sample inlet, such as a microGC system described in Bhushan A et al., "Hybrid integration of injector and detector functions for microchip gas chromatography," *Analyst* 2010; 135:2730-6; Lewis P R et al., "Recent advancements in the gas-phase Micro Chem Lab," *IEEE Sens. J.* 2006 June; 6(3):784-95; Manginell R P et al., "A monolithically-integrated μGC chemical sensor system," *Sensors* 2011; 11:6517-32; Lewis A C et al., "Microfabricated planar glass gas chromatography with photoionization detection," *J. Chromatogr. A* 2010; 1217:768-74; Whiting J J et al., "High-speed two-dimensional gas chromatography using microfabricated GC columns combined with nano-electromechanical mass sensors," *Int'l Solid-State Sensors, Actuators and Microsystems Conf.*, held on 21-25 Jun. 2009 in Denver, Colo., pp. 1666-9, as well as U.S. Pat. Nos. 6,666,907, 6,699,392, and 8,123,841, each of which is incorporated herein by reference in its entirety); a tunable UV source; a preconcentrator (e.g., those in Manginell R P et al., "Mass-sensitive microfabricated chemical preconcentrator," *J. Microelectromech. Sys.* 2008 December; 17(6): 1396-407, which is incorporated herein by reference in its entirety); a tube, such as that described in U.S. Pat. No. 7,155,812, which is incorporated herein by reference in its entirety; a thermionic detector, such as that described in U.S. Pat. No. 8,298,488, which is incorporated herein by reference in its entirety, or any other useful component.

Materials

The detector and system herein can be formed with any useful material. For instance, the electrodes can be formed from a conductive material, the insulator from an insulative material, and the housing, if present, from an inert material. Exemplary materials include an insulative material, e.g., ceramic, alumina, ceria, polytetrafluoroethylene, or dielectric; a conductive material, e.g., a metal, stainless steel, steel, titanium, aluminum, copper, nickel, chromium, tungsten, or alloys thereof, as well as any substrate or material described in U.S. Pat. No. 6,444,326, which is incorporated herein by reference in its entirety; or an inert material, e.g., stainless steel. In particular embodiment, the surface of the material is passivated. For instance, passivation for stainless steel can include an amorphous silicon coating or a Siltek® coating, such as that described in U.S. Pat. No. 6,444,326, which is incorporated herein by reference in its entirety.

Uses and Analytes

The detectors and systems herein can be employed for any useful purpose. For instance, the detector can be employed to detect one or more analytes in a sample (e.g., a GC sample). Exemplary analytes include one or more of the following: light gases (e.g., hydrogen ($H_2$), methane ($CH_4$), carbon dioxide ($CO_2$), or carbon monoxide (CO), or any greenhouse gas (GHG)); volatile organic compounds (VOCs, e.g., from any source, such as microorganisms, pathogens, humans, toxic industrial chemicals (TICs), solvents, fixed/permanent gases, explosives, GHG, water contaminants, and/or chemical and biological warfare agents (CWAs and BWAs)), such as acids (e.g., isovaleric acid), aldehydes (e.g., acetaldehyde or 3-methylbutanal), ketones (e.g., acetoin or 2-nonanone), hydrocarbons (e.g., 2-butene or 1,10-undecadiene), alcohols (e.g., 2-methyl-1-propanol, 2-butanol), esters (e.g., ethyl formate or methyl 2-methylbutyrate), aromatics (e.g., benzene or toluene), including volatile nitrogen compounds (e.g., methylpyrrole), and volatile sulfur compounds (e.g., dimethylsulfide); semi-volatile organic compounds; human-specific volatile signals (e.g., hexenoic acid, such as 3-methyl-2-hexenoic acid or (E)-3-methyl-2-hexenoic acid; volatile signatures of pathogens (e.g., bacteria, fungi, food pathogens, or biological warfare agents, such as *Salmonella, Staphylococcus* (e.g., *S. aureus*), *Bacillus* (*B. anthracis*), *Mycobacteria* (e.g., *M. bovis* or *M. tuberculosis*), *Pseudomonas* (e.g., *P. aeruginosa*), *Neisseria* (e.g., *N. meningitidis*), *Streptococcus* (e.g., *S. pneumoniae*), *Klebsiella* (e.g., *K. oxytoca*), *Salmonella, Acinetobacter* (e.g., *A. baumannii*), *Enterobacter* (e.g., *E. cloacae*), *Penicillium* (e.g., *P. brevicompactum*), *Proteus* (e.g., *P. vulgaris*), *Serratia* (e.g., *S. marcescens*), *Yersinia* (e.g., *Y. pestis*), or *Escherichia* (e.g., *E. coli*)) and diseases in livestock and humans (e.g., acetaldehyde, acetic acid, acetone, acetonitrile, amine, 2-aminoacetophenone, butadiene, 1-butanol, 2-butanone, 1-decanol, dimethyl disulfide, dimethyl sulfide, ethanol, ethylene glycol, formaldehyde, hexanal, hydrogen sulfide, indole, isobutanol, isopentanol, 9-isopentanol, isopentyl acetate, isoprene, methanethiol, methanol, methyl p-anisate, 2-methyl-1-butanol, methyl nicotinate, 4-methylphenol, methyl phenylacetate, 2-nonanone, pentanol (including any isomer thereof), 2-pentanone, o-phenyl anisole, propanol, propene, pyrimidine, toluene, or trimethylamine); pesticides; water contaminants, e.g., trihalomethanes; explosives-related compounds (e.g., 2,3-butanediol, n-decane, dicyclohexylamine, 2,6-dimethylaniline, 2,6-dimethylphenol, 2,3-dimethyl-2,3-dinitrobutane (DMNB), 2-ethylhexanoic acid, methyl decanoate, methyl dodecanoate methyl undecanoate, nitrobenzene, 2-nitrotoluene, 3-nitrotoluene, nonanal, 1-octanol, triacetone triperoxide (TATP), or n-undecane); or chemical warfare agents (CWAs), e.g., dimethyl methylphosphonate (DMMP) in any sample (e.g., in soil, water, breath, saliva, food, liquid, milk, etc.), as well as gaseous or GC processed forms of any of these samples.

Other analytes and VOCs are described in Mainelis G et al., "Performance characteristics of the aerosol collectors of the Autonomous Pathogen Detection System (APDS)," *Aerosol Sci. Technol.* 2005; 39:461-71; Akutsu T et al., "Individual comparisons of the levels of (E)-3-methyl-2-hexenoic acid, an axillary odor-related compound, in Japanese," *Chem. Senses* 2006 May; 31:557-63; McNerney R et. al., "Production of volatile organic compounds by mycobacteria," *FEMS Microbiol. Lett.* 2012; 328:150-6; Bostaris G et. al., "Rapid detection methods for viable *Mycobacterium avium* subspecies paratuberculosis in milk and cheese," *Int. J. Food Microbiol.* 2010; 141:S87-90; Biet F et al., "Zoonotic aspects of *Mycobacterium bovis* and *Mycobacterium avium-intracellulare* complex (MAC)," *Vet. Res.* 2005; 36:411-36; Syhre M et al. "The scent of *Mycobacterium tuberculosis,*" *Tuberculosis* 2008; 88:317-23; Syhre M et al., "The scent of *Mycobacterium tuberculosis*—Part II breath," *Tuberculosis* 2009; 89:263-6; Straus E et al., "Radioimmunoassay of tuberculoprotein derived from *Mycobacterium tuberculosis,*" *Proc. Nat'l Acad. Sci. USA* 1980 July; 77:4301-4; Spooner A D et al., "Evaluation of a combination of SIFT-MS and multivariate data analysis for the diagnosis of *Mycobacterium bovis* in wild badgers," *Analyst* 2009; 134:1922-7; Harris N B et al., "Recovery of *Mycobacterium bovis* from soft fresh cheese originating in Mexico," *Appl. Environ. Microbiol.* 2007 February; 73:1025-8; Laurens J B et al., "Gas chromatographic analysis of trace gas impurities in tungsten hexafluoride," *J. Chromatogr. A* 2001; 911:107-12; Roberge M T et al., "Evaluation of the pulsed discharge helium ionization detector for the analysis of hydrogen and methane in breath," *J. Chromatogr. A* 2004; 1027:19-23; Forsyth D S et al., "Detection of organotin, organomercury, and organolead compounds with a pulsed discharge detector (PDD)," *Anal. Bioanal. Chem.* 2002; 374:344-7; Int. Pub. No. WO 2009/045116; Gibson T et al., "Not to be sniffed at," *Microbiol. Today* 2000 February; 27:14-17; Adamovics J A et al., "Gas Chromatography," Chapter 4 in *Chromatographic analysis of pharmaceuticals,* 2nd edition, Adamovics J A (ed.), 1997, Marcel Dekker, Inc., New York, N.Y., pp. 79-134; Ross B M et al., "Stability of methylnicotinate in aqueous solution as utilized in the 'niacin patch test'," *BMC Res. Notes* 2008 September; 1:89 (5 pp.); Achyuthan K E et al., "Design considerations for high-throughput screening and in vitro diagnostic assays," *Comb. Chem. High Throughput Screen.* 2007 July; 10(6):399-412; Jünger M et al., "Ion mobility spectrometry for microbial volatile organic compounds: A new identification tool for human pathogenic bacteria," *Appl. Microbiol. Biotechnol.* 2012 March; 93(6): 2603-14; Dolch M E et al., "Volatile compound profiling for the identification of Gram-negative bacteria by ion-molecule reaction-mass spectrometry," *J. Appl. Microbiol.* 2012; 113: 1097-105; Filipiak W et al., "Molecular analysis of volatile metabolites released specifically by *Staphylococcus aureus* and *Pseudomonas aeruginosa,*" *BMC Microbiol.* 2012; 12:113 (16 pp.); Allardyce R A et al., "Detection of volatile metabolites produced by bacterial growth in blood culture media by selected ion flow tube mass spectrometry (SIFT-MS)," *J. Microbiol. Meth.* 2006; 65:361-5; Zhu J et al., "Fast detection of volatile organic compounds from bacterial cultures by secondary electrospray ionization-mass spectrometry," *J. Clin. Microbiol.* 2010; 48:4426-31; Bunge M et al., "On-line monitoring of microbial volatile metabolites by proton transfer reaction-mass spectrometry," *Appl. Environ. Microbiol.* 2008 April; 74(7):2179-86; Senecal A G et al., "Rapid detection of pathogenic bacteria by volatile organic compound (VOC) analysis," *Proc. SPIE* 2002; 4575:121-31; Grob K, Jr. et al., "Comprehensive, standardized quality test for glass capillary columns," *J. Chromatogr.* 1978; 156:1-20; Grob K et al., "Testing capillary gas chromatographic columns," *J. Chromatogr.* 1981; 219:13-20; and Manginell R P et al., "Diagnostic potential of the pulsed discharged helium ionization detector (PDHID) for pathogenic Mycobacterial volatile biomarkers," *J. Breath Res.* 2013; 7:037107 (9 pp.), each of which is incorporated herein by reference in its entirety.

EXAMPLE

Example 1: Human Cargo Detection Via a Microfabricated Pulsed-Discharge Ionization Detector We selected the pulsed discharge ionization detector (PDID) for the sniffing volatile and/or semi-volatile organic compounds (VOCs) in order to detect microorganisms, humans, toxic industrial chemicals (TICs), solvents, fixed/permanent gases, explosives, greenhouse gas (GHG), potable water contaminants, and chemical and biological warfare agents (CWA and BWA).

Toward this end, we have developed an array of micro-instrumentation components including preconcentrator (PC), gas chromatography (GC) columns, and valves (see, e.g., Manginell R P et al., "A monolithically-integrated μGC chemical sensor system," *Sensors* 2011; 11:6517-32; Manginell R P et al., "A materials investigation of a phase-change micro-valve for greenhouse gas collection and other potential applications," *Rev. Sci. Instrum.* 2012; 83:031301 (11 pp.); and Galambos P et al., "Active MEMS valves for flow control in a high-pressure micro-gas-analyzer," *J. Microelectromech. Sys.* 2011 October; 20(5):1150-62).

In the context of detectors, we found the PDID to be versatile as a rugged, non-destructive, low power, portable detector of volatiles emerging from GC columns without the need for a vacuum pump (Forsyth D S, "Pulsed discharge detector: theory and applications," *J. Chromatogr. A* 2004; 1050:63-8). The PDID can be operated in at least two modes, including a pulsed discharge helium (He) ionization detector (PDHID) mode and pulsed discharge electron capture detector (PDECD) mode.

The first mode, PDHID, combines many attractive features including universal and selective detection with the advantage of not requiring radioactive materials for effecting ionization of compounds prior to detection (Gremaud G et al., "Windowless pulsed-discharge photoionization detector application to qualitative analysis of volatile organic compounds," *J. Chromatogr. A* 1996; 724:235-50; and Wentworth W E et al., "Pulsed discharge emission detector: an element-selective detector for gas chromatography," *J. Chromatogr. A* 2000; 872:119-40).

In PDHID, photons are generated in a He AC plasma discharge, and these photons photoionize the sample or analytes eluting from a GC column. The Hopfield emission band of He produces photons with an energy interval of 13.5 to 17.7 eV, which is sufficiently high to ionize almost all compounds, with the exception of neon (Ne). These electrons are directed towards the collector electrode disposed between two twin bias electrodes, and the ensuing changes to the current enables detection of a wide range of compounds including explosives, drugs, pesticides, elements, and volatiles with exquisite sensitivity in the femtogram range (Forsyth D S, *J. Chromatogr. A* 2004; 1050:63-8). The PDID is thus an ideal detector, being commercially available, non-radioactive, non-destructive, requiring low-power, with an already small footprint and capable of further miniaturization (Winniford B L et al., "Universal and discriminative detection using a miniaturized pulsed discharge detector in comprehensive two-dimensional GC,"*J. Sep. Sci.* 2006; 29:2664-70) in order for its adaptation into a field-portable sniffer system.

The second mode, PDECD, uses the same photoionization method as above and the hardware is actually the same as that for PDHID. However, one of the bias electrodes is connected to the electrometer, the collector electrode is not used, while the other bias electrode still provides bias. In this mode, the baseline current is monitored. When an electronegative species, such as explosives or nitrogen- or phosphorous-containing organic molecules, enter through the GC, they scavenge baseline electron current. The signal for electronegative compounds is thus seen as a reduction in baseline current.

The present application includes a miniaturized PDID (miniPDID) capable of detecting any mode, including PDHID and PDECD modes. An exemplary miniPDID is provided in FIG. 4A. This scaled prototype is about 10 cm$^3$ in volume as compared to the commercial predecessor at >400 cm$^3$. The central, active channel or chamber of the baseline prototype design had the same internal diameter as the commercial predecessor (3 mm) but at 17.5 mm in length is ~40% as long as its predecessor. Our detector cell volume was 100 microliters compared to a commercial version of 127 microliters with a comparable time to sweep a peak from the detector cell (170 milliseconds for our prototype, compared to 127 milliseconds for the commercial unit).

Design

Rapid prototyping techniques were used to speed manufacture and also to allow for design variations with 1.5 mm internal diameter and/or one quarter the length of the commercial system. Miniaturization is very important from the standpoint of creating a portable system and reducing power consumption and detector dead volume to our handheld prototype for field testing. Described herein are experiments designed to understanding the impact of miniaturization (e.g., scaling effects) and how to optimize gas flow rates, voltage biases and the GC outlet position.

The solid models of FIGS. 3 and 4A allows the central, active channel or chamber of the miniPDID to be visualized. The white cylindrical parts are machined annular ceramic (e.g., 99.6% alumina) insulators, which, together with the dark gray annular electrodes, which together create the central flow channel. The insulators are chemically inert and electrically isolate the bias, signal, and HV electrodes from one another.

Our custom electrode designs were rapid prototyped from stainless steel using photochemical etching at Vacco, Inc. Stainless steel was chosen for its relative chemical inertness. The stainless steel surface could be passivated further through a variety of commercial processes, such as the Silco Steel® method for superior inertness. This unique electrode design allows for nesting of the insulators so the overall core of the detector can be self-aligned and compressed together in assembly. The electrodes also incorporate a tang for insertion into standard circuit board spring connectors (Mill-Max model 0342). This method of manufacture allows for close spacing of the electrodes for miniaturization and robust, inexpensive manufacture.

FIG. 4A illustrate other features of our design. The structure is made from stainless steel for relative chemical inertness. The stainless could be passivated further through a variety of commercial processes, such as the Silco Steel® method.

There are three fluidic connections to the detector: the helium inlet, the GC inlet, and the vent or exhaust. For this prototype, these connections were made in the two end caps or ports using commercial swage fittings (Valco/VICI, Houston, Tex.) designed specifically for GC applications. In fact, the ground pin for the HV plasma discharge was also installed through the same type of swage fitting. This approach allowed the axial depth of the ground pin to be varied and then locked into place by swaging. For the work described herein, the ground pin was fixed at the centroid of the HV electrode bore.

The use of commercial GC fittings simplified GC connections in the first prototype, but also set a minimum size scale for the end caps. As mentioned below, future generations of the PDID can be made significantly smaller (e.g., AA battery size) simply by welding miniature stainless steel tubing to the detector housing for fluidic connections.

Mesoscopic electrical connections to the miniPDID were made using four standard SubMiniature version C (SMC) connectors to a custom ceramic circuit board. SMC connectors were chosen for simplicity of connectivity to laboratory instruments. In the future, a single miniature 4-pin connector with bias, signal, ground, and HV lines can be purchased from suppliers such as Positronics to reduce the total connector size to about one fourth of the present size. The custom ceramic circuit board can easily withstand temperatures of 150° C. and higher, which could be needed for certain detector applications.

Testing

The miniPDID test setup included a laptop running Labview software for data acquisition from the commercial Keithley 6487 Picoammeter. The detector was placed in a commercial Agilent 5890 GC oven for ease of GC connectivity and temperature control. The bias voltage was provided by either a Stanford Research Systems P350 supply or a Pacific Design Power 2k-15 supply. HV pulsing was provided by a Valco supply similar to that provided with the D-2 system.

For diagnostic purposes, a custom-made and calibrated inductive pickup was created to examine the voltage and current delivered by the HV supply to the helium plasma. In initial experiments, a Hamamatsu Photo Multiplier Tube (PMT) was coupled to the miniPDID using an Ocean Optics optical fiber coupling system with a custom-made lens holder adapter. A Tektronics MS03054 Oscilloscope was used to capture the PMT and pickoff signals. The PMT apparatus was not used during GC/detection experiments, but only for initial plasma diagnostics. In one instance, the HV pulse train had a frequency of about 4 kHz with a photo-emission duty cycle of about 40%, conditions which provided sufficient signal without overheating and sputtering the HV and ground electrodes. The maximum peak voltages during plasma ignition were roughly +/−325 V.

Figure 12:
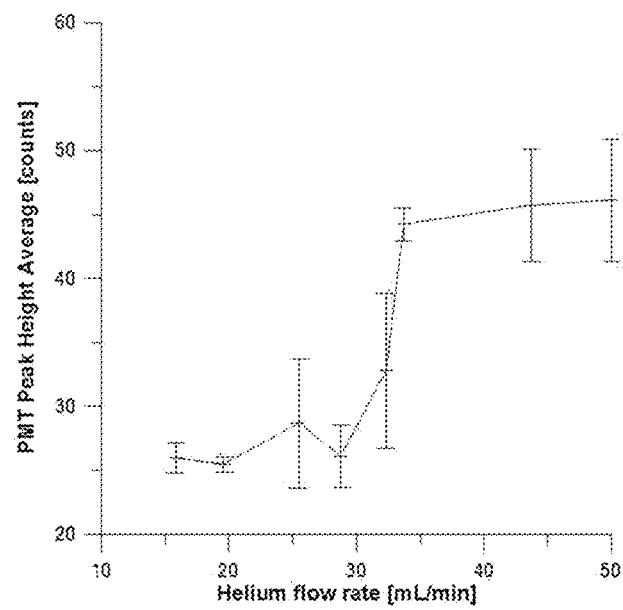
FIG. 12 is a graph showing plasma light output as a function of helium gas flow rate. Three PMT measurements were taken at each flow rate and averaged. The error bars were set by the standard deviation. The light output stabilized above 35 mL/min.

The peak number of counts from the PMT was measured as a function of helium flow rate into the miniPDID to understand the light emission intensity dependence on helium flow. Three samples were taken at each flow rate, and the average and standard deviation were calculated and plotted in FIG. 12. The light output from the plasma, which was used to photoionize chemical analytes eluting from the GC, stabilized above about 35 mL/min. For the remainder of the experiments, the helium flow was set between 35-45 mL/min.

Results

Figure 13:
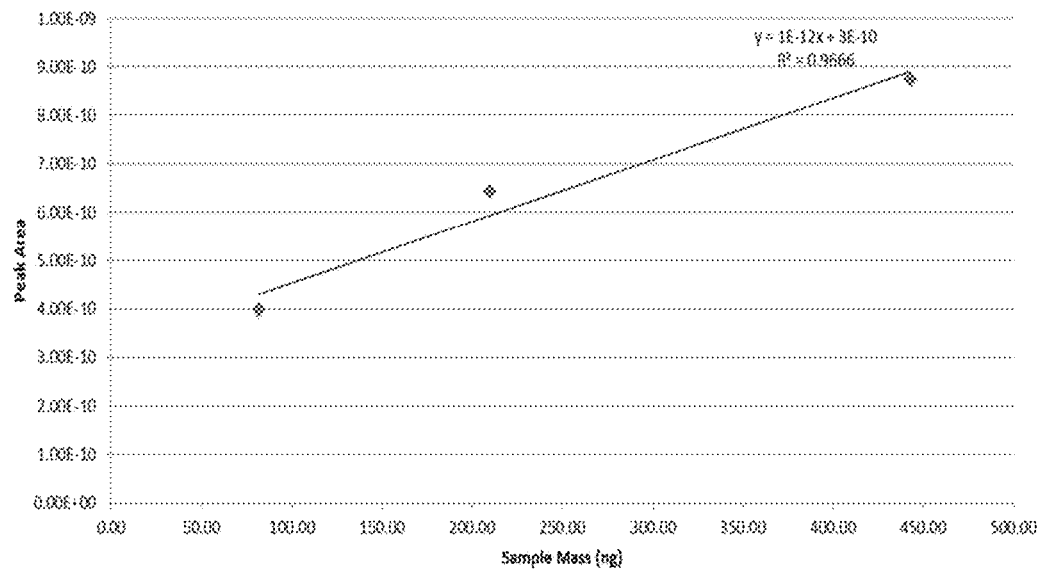
FIG. 13 is a graph showing un-optimized miniPDID response to hexenoic acid. The actual peak areas are shown in the inset in units of A·s.

For an initial test of performance, we studied the sensitivity of the miniPDID to 3-methyl-2-hexenoic acid for comparison with the D-2 data for the commercial system. For this test, the GC outlet was positioned roughly at the centroid of the collector electrode, the bias voltage was set at −25V, and the GC head pressure at 15 psi. The data are shown in FIG. 13.

Subsequent experimentation has shown that the conditions used for this experiment were non-optimal and relocating the GC outlet, increasing the GC flow, and increasing the negative bias could increase the sensitivity by at least a factor of 25 in composite. As noted above, even the un-optimized performance of our miniPDID was within striking distance of the performance of a commercial unit. Thus, the commercial D-3 unit sensitivity for 3-methyl-2-hexenoic acid was estimated at 5.7 nanograms, as compared to the miniPDID un-optimized sensitivity of 18 nanograms. With the anticipated 25-fold improvement in sensitivity following optimization of the miniPDID settings, its sensitivity will likely be less than 1 nanogram. In sine embodiments, the optimized sensitivity of the miniPDID could be 6-10-fold higher than the commercial D-3 unit with a 40-fold reduction in footprint. These data provide a proof-of-concept demonstration of the functionality of the miniPDID for sensing indicators of human presence, which can be repeated using optimized conditions according to the procedures described next.

This provided a proof of concept demonstration of the functionality of the miniPDID for sensing indicators of human presence, which can be repeated using optimized conditions according to the procedures described next. To understand scaling and optimization of the detector, we chose pentane as a target analyte, which has a well-known ionization cross-section for modeling.

Auto-injections of 1 µL of pentane were used as a standard for our analyses. Experiments include changing the bias magnitude (from 0 to −100 V) and the GC head pressure (15 psi, 20 psi, or 35 psi). Overall, when the GC outlet was placed in Position '1' (see FIG. 4B for position locations), the bias magnitude provided a minimal difference. In addition, the higher GC head pressure of 20 psi provided about six times greater signal height, as compared to the lower GC head pressure of 15 psi. While using a GC head pressure of 35 psi produced faster elution times, the peak area was reduced relative to the 20 psi case, possibly because peak rise times exceeded reasonable data acquisition rates. Accordingly, placement of the GC connector or outlet, as well as GC head pressure, and bias voltages can be modified to obtain optimal data acquisition and sensitivity ranges.

GC peak area, width (full width at half maximum, FWHM), and peak height were next studied as a function of bias and GC position for the case with a 20 psi GC pressure head. Generally, the performance measured in terms of peak area increases with bias and as the GC proceeds further into the detector up to a maximum at about Position '−3' (see, FIG. 4B). FWHM also generally increased with bias voltage at a given position, meaning that arbitrarily increasing the bias to increase the peak area could begin to degrade chromatography separation performance.

Figure 14:
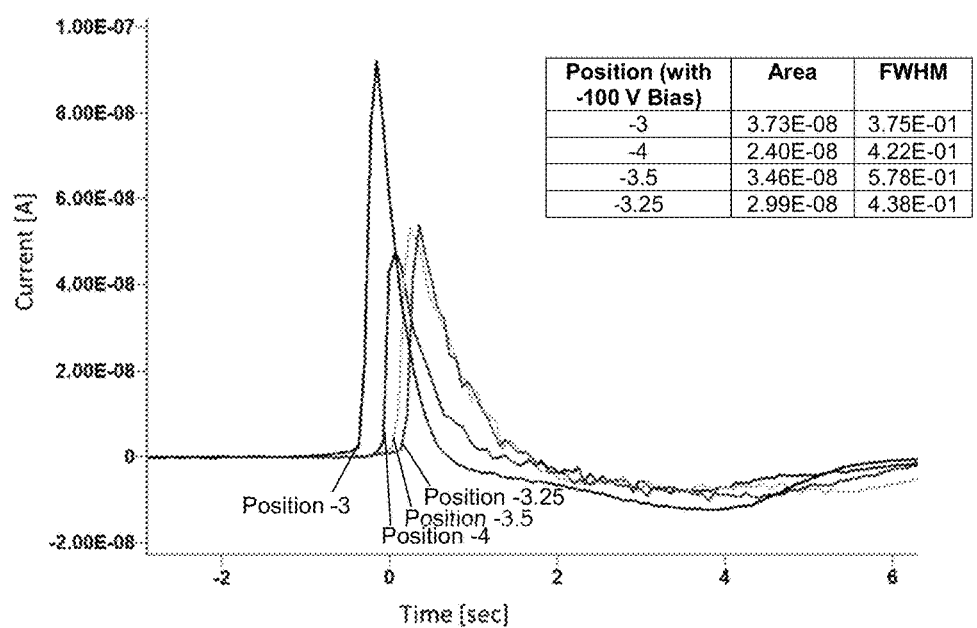
FIG. 14 is a graph showing peak area and FWHM at Position '−3' and −100V bias. Position '−3' had the best performance with pentane as a model analyte.

The response at −100V bias for Position −3 and beyond (i.e., the GC ever closer to HV source) is provided in FIG. 14. This data, and data on Positions 1' to '−2' (not shown herein), indicate that for pentane and 20 psi pressure head, Position '−3,' which was slightly left of the leftmost bias electrode in FIG. 4B, provided the best response using pentane as the model analyte. For this position, the FWHM at −50 V is roughly the same as at −100V, while the signal increases by about 22% in going to the larger negative bias.

The miniPDID has been impressively rugged, operating nearly continuously for nine months without a single failure. The present helium consumption rate for the plasma, which may be reduced in further miniaturized versions, can be accommodated in portable use with a 1" diameter by 5" long cylinder. This cylinder volume would allow operation for over 9 hours, which is 3 hours longer than battery life for our portable systems. The benefits of including a miniature helium tank and miniPDID are near universal detection at sub-part per billion (ppb) to parts per trillion (ppt) levels, as well as ruggedness and non-fouling performance.

Modeling of the electron trajectories within the miniPDID was initiated using the SIMION software modeling package. Initial work evaluated the time required to complete a model of 100 electrons born at the various GC column positions. For the GC Position '0' and a bias of −50V, for example, the model showed that the electrons move in trajectories that are quasi-stable in the region of the collector resulting in long simulation times. However, based on histograms of electron position, approximately 50% of the electrons escaped the modeling volume rather than being collected. Additional design improvements can be predicted by modeling and implemented to further increase the sensitivity of the miniPDID.

CONCLUSION

Despite the dramatic 40-fold reduction in size for the Sandia miniPDID, the performance metrics were comparable. Thus, the un-optimized sensitivity of the miniPDID was barely 3-fold lower compared to its commercial counterpart for the detection of the human-specific volatile compound, 3-methyl-2-hexenoic acid. We are confident that after optimization of gas flow rates, voltage biases, and GC outlet position, this gap will be bridged and sensitivity will be improved.

The simplicity, universality, and sub-ppb response of the PDID detector is very attractive. It does not require a vacuum pump like mass spectrometers, and both miniature vacuum pumps and mass spectrometers are years, perhaps decades, away from readiness for handheld use. Unlike other photoionization detectors, the PDID is universal (but can be made specific) and has no UV windows to foul or limit performance. The miniPDID will run for 9 hours on a miniature 1" diameter×5" He tank, which is three hours longer than the battery life in our portable systems. Simple changes, such as the use of welded tubing, smaller connectors and reduced housing size can reduce the detector down to the size of an AAA battery or smaller. The miniPDID herein can be coupled with any useful microGC systems for handheld, sub-ppb and ppt multi-threat detection of toxic chemicals, water contaminants, chemical warfare agents, explosives, biological volatiles, light gases, and disease indicators, among more general chemical detection uses.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A miniaturized pulsed discharge ionization detector comprising:
   an ionization source configured to provide a discharge zone disposed in a portion of a chamber of the detector;
   a first annular electrode comprising a first proximal face, a first distal face, a first tang, and a first bore defined therethrough the first proximal and first distal faces,
      wherein each of the first proximal and the first distal faces comprises a first recessed portion disposed around the first bore and a first ridge portion disposed around the first recessed portion, and
      wherein the first tang extends continuously from the first ridge portion and comprises an elongated structure configured to be inserted directly into a connector of a circuit board;
   a first annular insulator comprising a second proximal face, a second distal face, and a second bore defined therethrough the second proximal and second distal faces,
      wherein at least one of the second proximal and the second distal faces is configured to nest within at least one of the first recessed portions of the first annular electrode; and
   a second annular insulator comprising a third proximal face, a third distal face, and a third bore defined therethrough the third proximal and the third distal faces,
      wherein at least one of the third proximal and the third distal faces is configured to nest within at least one of the first recessed portions of the first annular electrode,
   wherein the first annular electrode is disposed between the first and second annular insulators, and
   wherein the bores of each of the first annular electrode, first annular insulator, and second annular insulator is configured to provide at least a portion of the chamber of the detector.

2. The detector of claim 1, further comprising a positioner that comprises a fourth proximal face, a fourth distal face, and a fourth bore defined therethrough the fourth proximal and the fourth distal faces, wherein the positioner is located distal to the ionization source.

3. The detector of claim 1, further comprising a second annular electrode comprising a fourth proximal face, a fourth distal face, a fourth tang, and a fourth bore defined therethrough the fourth proximal and the fourth distal faces,
   wherein each of the fourth proximal and the fourth distal faces comprises a second recessed portion disposed around the fourth bore and a second ridge portion disposed around the second recessed portion, and
   wherein the fourth tang extends continuously from the second ridge portion, and
   wherein at least one of the fourth proximal and the fourth distal faces of the second annular insulator is configured to nest within at least one of the second recessed portions of the second annular electrode.

4. The detector of claim 3, wherein the fourth tang of the second annular electrode comprises an elongated structure configured to be inserted directly into a connector of the circuit board.

5. The detector of claim 1, wherein the ionization source comprises a ground electrode and an annular high voltage (HV) electrode,
   wherein the HV electrode comprises a proximal face, a distal face, a tang, and a bore defined therethrough the proximal and distal faces,
      wherein each of the proximal and distal faces comprises a recessed portion disposed around the bore and a ridge portion disposed around the recessed portion, and wherein the tang extends from the ridge portion, and
      wherein the bore of the HV electrode, with the bore of each of the first annular electrode, first annular insulator, and second annular insulator, is configured to provide at least a portion of the chamber of the detector; and
   wherein at least a portion of the ground electrode is disposed proximal to or within the bore of the HV electrode, thereby providing the discharge zone disposed in a portion of a chamber of the detector.

6. The detector of claim 5, further comprising a proximal port comprising an electrode inlet and a discharge gas inlet, wherein the electrode inlet is configured to position the ground electrode within the chamber.

7. The detector of claim 6, further comprising a distal port comprising a sample inlet and a vent, wherein the sample inlet is configured to position a GC connector within the chamber.

8. The detector of claim 7, further comprising a circuit board configured to receive the first tang of the first annular electrode and the annular HV electrode.

9. The detector of claim 5, wherein the tang of the HV electrode comprises an elongated structure configured to be inserted directly into a connector of the circuit board.

10. The detector of claim 1, wherein the connector is a spring connector.

11. The detector of claim 1, wherein the first annular electrode comprises a rapid prototyped conductive material.

12. A miniaturized pulsed discharge ionization detector comprising:
an ionization source configured to provide a discharge zone disposed in a portion of a chamber of the detector;
a plurality of annular electrodes, wherein each electrode comprises a first proximal face, a first distal face, a first tang, and a first bore defined therethrough the first proximal and the first distal faces,
wherein each of the first proximal and the first distal faces comprises a first recessed portion disposed around the first bore and a first ridge portion disposed around the first recessed portion, and
wherein the first tang extends continuously from the first ridge portion and comprises an elongated structure configured to be inserted directly into a connector of a circuit board; and
a plurality of annular insulators comprising a second proximal face, a second distal face, and a second bore defined therethrough the second proximal and the second distal faces,
wherein each of the second proximal and the second distal faces is configured to nest within at least one of the recessed portions of at least one annular electrode;
wherein at least one annular electrode is disposed between the two annular insulators, and
wherein the bores of each of the annular electrodes and annular insulators is configured to provide at least a portion of the chamber of the detector.

13. The detector of claim 12, wherein the plurality of annular electrodes comprises n annular electrodes, and the plurality of annular insulators comprises n+x annular insulators, wherein n is an integer selected from 1 to 10 and x is an integer selected from 0 to 10.

14. The detector of claim 13, wherein the ionization source comprises a ground electrode and an annular high voltage (HV) electrode,
wherein the annular HV electrode comprises a third proximate face, a third distal face, a third tang, and a third bore defined therethrough the third proximal and the third distal faces,
wherein each of the third proximal and the third distal faces comprises a second recessed portion disposed around the third bore and a second ridge portion disposed around the second recessed portion, and
wherein the third tang extends continuously from the second ridge portion and comprises an elongated structure configured to be inserted directly into a connector of a circuit board, and
wherein the third bore of the annular HV electrode, with the bores of each of the first annular electrode, first annular insulator, and second annular insulator, is configured to provide at least a portion of the chamber of the detector;
wherein at least a portion of the ground electrode is disposed proximal to or within the bore of the annular HV electrode, thereby providing the discharge zone disposed in a portion of a chamber of the detector; and
wherein the ionization source is located proximal to the n annular electrodes and n+1 annular insulators.

15. The detector of claim 14, further comprising a first positioner that comprises a fourth proximal face, a fourth distal face, and a fourth bore defined therethrough the fourth proximal and the fourth distal faces,
wherein the first positioner is located distal to the ionization source, and
wherein the fourth bore of the position, with each of the annular electrodes and annular insulators, is configured to provide at least a portion of the chamber of the detector.

16. The detector of claim 15, further comprising a second positioner that comprises a fifth proximal face, a fifth distal face, and a fifth bore defined therethrough the fifth proximal and the fifth distal faces.

17. The detector of claim 16, further comprising a proximal port comprising an electrode inlet and a discharge gas inlet, wherein the electrode inlet is configured to position the ground electrode within the chamber; and a distal port comprising a sample inlet and a vent, wherein the sample inlet is configured to position a connector within the chamber.

18. The detector of claim 17, further comprising a circuit board having a plurality of connectors, wherein each connector is configured to receive one of the tangs of each of the annular electrodes and the annular HV electrode.

19. The detector of claim 18, further comprising an external housing configured to house a core comprising the plurality of annular electrodes and annular insulators, wherein the external housing attaches reversibly to the circuit board.

20. The detector of claim 13, wherein each annular electrode is disposed between two annular insulators.

21. A non-radiation ionization source comprising a ground electrode and an annular high voltage (HV) electrode,
wherein the annular HV electrode comprises a first proximate face, a first distal face, a first tang, and a first bore defined therethrough the first proximal and the first distal faces,
wherein each of the first proximal and the first distal faces comprises a first recessed portion disposed around the first bore and a first ridge portion disposed around the first recessed portion, and
wherein the first tang extends continuously from the first ridge portion and comprises an elongated structure configured to be inserted directly into a connector of a circuit board, and
wherein at least a portion of the ground electrode is disposed proximal to or within the first bore of the annular HV electrode, thereby providing a discharge zone.

22. The ionization source of claim 21, further comprising a discharge gas inlet located in proximity to the annular HV electrode and configured to provide a discharge gas to the discharge zone.

23. The ionization source of claim 22, wherein the discharge gas is a plasma gas selected from the group consisting of helium, argon, krypton, hydrogen, $CO_2$, $NH_3$, $N(CH_3)_3$, $CH_4$, nitrogen, and xenon; or an excimer gas selected from the group consisting of $F_2$, $Ar_2$, $Kr_2$, $Xe_2$, ArF, ArCl, ArBr, KrF, KrCl, XeBr, XeCl, and XeF.

24. The ionization source of claim 22, wherein a flow rate of the discharge gas is greater than a flow rate of test analyte.

25. The ionization source of claim 21, wherein the ground electrode comprises a pin electrode.

26. The ionization source of claim 21, further comprising a gate located between the discharge zone and a detection zone, wherein the gate is connected to a gate drive circuit configured to deliver a gating function to the gate.

27. A miniaturized pulsed discharge ionization detector comprising:
- a circuit board comprising a plurality of connectors;
- an ionization source configured to provide a discharge zone disposed in a portion of a chamber of the detector;
- a plurality of annular electrodes, wherein each electrode comprises a first proximal face, a first distal face, a first tang, and a first bore defined therethrough the first proximal and the first distal faces,
  - wherein each of the first proximal and the first distal faces comprises a first recessed portion disposed around the first bore and a first ridge portion disposed around the first recessed portion, and
  - wherein the first tang extends continuously from the first ridge portion and comprises an elongated structure configured to be inserted directly into one of the plurality of connectors of the circuit board; and
- a plurality of annular insulators comprising a second proximal face, a second distal face, and a second bore defined therethrough the second proximal and the second distal faces,
  - wherein each of the second proximal and the second distal faces is configured to nest within at least one of the recessed portions of at least one annular electrode;
- wherein at least one annular electrode is disposed between the two annular insulators, and
- wherein the bores of each of the annular electrodes and annular insulators is configured to provide at least a portion of the chamber of the detector.

* * * * *